United States Patent [19]
Murakami et al.

[11] 3,953,428
[45] Apr. 27, 1976

[54] AMPICILLIN DERIVATIVES SUBSTITUTED BY HETEROCYCLIC ACYL GROUP

[75] Inventors: Masuo Murakami, Tokyo; Ichiro Isaka; Akio Koda, both of Hoya; Norio Kawahara; Teruya Ashiwagi, both of Ageo; Yukiyasu Murakami, Urawa; Kuniichiro Yano, Tokorozawa; Kohzi Nakano, Shiraoka; Isao Souzo, Urawa, all of Japan

[73] Assignee: Yamanouchi Pharmaceutical Co., Ltd., Tokyo, Japan

[22] Filed: May 1, 1973

[21] Appl. No.: 356,120

[30] Foreign Application Priority Data
May 8, 1972 Japan............ 47-45118
Aug. 21, 1972 Japan............ 47-83424
Aug. 25, 1972 Japan............ 47-85102
Aug. 25, 1972 Japan............ 47-85103
Dec. 15, 1972 Japan............ 47-125952
Feb. 18, 1973 Japan............ 48-19917
Apr. 4, 1973 Japan............ 48-38132

[52] U.S. Cl............... 260/239.1; 424/271
[51] Int. Cl.² ................ C07D 499/44
[58] Field of Search ............ 260/239.1

[56] References Cited
UNITED STATES PATENTS
3,532,688  10/1970  Hatt et al............. 260/239.1
3,668,198  6/1972   Bernstein et al....... 260/239.1
3,711,471  1/1973   Kaplan et al.......... 260/239.1

Primary Examiner—Nicholas S. Rizzo
Attorney, Agent, or Firm—Burgess, Ryan and Wayne

[57] ABSTRACT

The ampicillin derivatives represented by the general formula

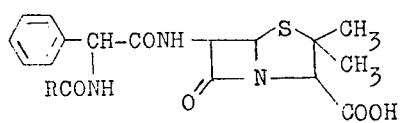

wherein R represents (1)

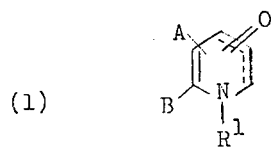

wherein R' represents a hydrogen atom, a methyl group, or an ethyl group and A and B each represents a hydrogen atom, a hydroxyl group, a methyl group, a methoxy group, a nitro group, or a halogen atom and further said B may combine with A on the carbon atom at the position to form

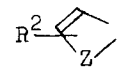

group (where in Z represents —CH=N— or —CH=CH— and an R² represents a hydrogen atom, a hydroxyl group, a phenyl group, a methyl group, an ethyl group, a methoxy group, an ethoxyl group, a methylthio group, a trifluoromethyl group, a halogen atom, a nitro group, an acetyl group, an acetamido group, a ethoxycarbonyloxy group, or a methylsulfonyl group and further $R_2$ and

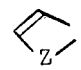

may form a thiazole, isothiazolo, pyrrolo, furo, or benzo fused ring which may be substituted by an oxo group, a methyl group, or an acetyl group) and the dotted line means an arbitrary double bond, (2)

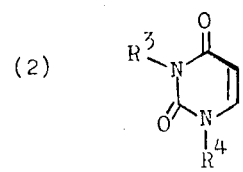

wherein $R^3$ and $R^4$ each represents a hydrogen atom or a methyl group, (3)

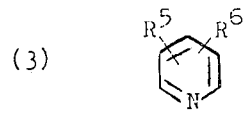

wherein $R^5$ represents a halogen atom, a methoxy group, a nitro group, or a hydroxyl group and $R^6$ represents a hydrogen atom, a methoxy group, a halogen atom, a nitro group, or a hydroxyl group, or (4)

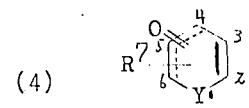

wherein $R^7$ represents a hydrogen atom or a hydroxyl group, Y represents O or S, and the dotted line means an arbitrary double bond, said substituent group, being bonded to the ampicillin molecule through —CO— at the 2-position, 3-position, 5-position or 6-position when the oxo group (+0) is at the 4-portion and being bonded to the ampicillin molecule through the —CO— group at the 2-position, 4-position, or 5-position when the oxy group is at the 6-position, and salts of the ampicillin derivatives.

Those compounds are valuable as antibacterial agents.

8 Claims, No Drawings

AMPICILLIN DERIVATIVES SUBSTITUTED BY HETEROCYCLIC ACYL GROUP

DETAILED DESCRIPTION OF THE INVENTION

The present invention relates to novel ampicillin derivatives. More particularly, the present invention relates to the compounds represented by the general formula

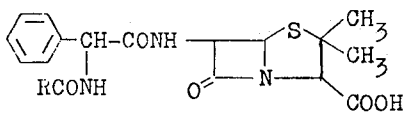

wherein R represents (1) 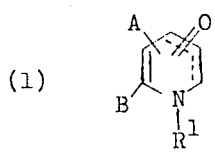

wherein $R^1$ represents a hydrogen atom. a methyl group, or an ethyl group and A and B each represents a hydrogen atom, a hydroxyl group a methyl group, a methoxy group, a nitro group, or a halogen atom and further said B may combine with A on the carbon atom at the 3-position to form an

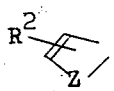

group (wherein Z represents —CH=N— or —CH=λ CH— and $R^2$ represents a hydrogen atom, a hydroxy group, a phenyl group, a methyl group, an ethyl group, a methoxy group, an ethoxy group, a methylthio group, a trifluoromethyl group, a halogen atom, a nitro group, an acetyl group, an acetamido group, an ethoxycarbonyloxy group, or a methylsulfonyl group and further $R^2$ may form together with

a thiazolo, isothiazolo, pyrrolo, furo, or benzo fused ring which may be substituted by an oxo group, a methyl group, or an acetyl group), and the dotted line means an arbitrary double bond, (2) 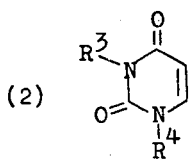

wherein $R^3$ and $R^4$ each represents a hydrogen atom or a methyl group, (3) 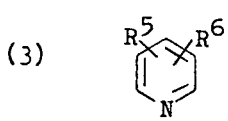

wherein $R^5$ represents a halogen atom, a methoxy group, a nitro group, or a hydroxy group and $R^6$ represents a hydrogen atom, a methoxy group, a halogen atom, a nitro group, or a hydroxy group, or (4) 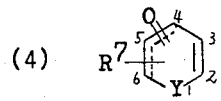

wherein $R^7$ represents a hydrogen atom or a hydroxy group, Y represents O or S, and the dotted line means an arbitrary double bond, said substituent group being bonded to the ampicillin molecule through a —CO— group at the 2-position, 3-position, 5-position, or 6-position when the oxo group (=O) is at the 4-position and being bonded to the ampicillin molecule through the -CO- group at the 2-position, 4-position, or 5-position when the oxo group (=O) is at the 6-position, and the salts thereof which are non-toxic and are useful as medicaments.

In addition, when $R^1$ of the dihydropyridine ring shown by the aforesaid formula (1) is a hydrogen atom or at least one of $R^3$ and $R^4$ of the tetrahydropyrimidine ring shown by the formula (2) is a hydrogen atom, it is possible to express the oxo group (=O) as a hydroxy group.

Those compounds are used as antibacterial agents for the prophylaxis and treatment of diseases of man and animal.

It is disclosed in the specification of U.S. Pat. No. 3,433,784 that compounds represented by the general formula

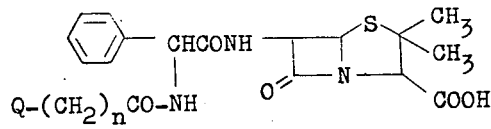

wherein Q represents a heterocyclic group which may be substituted and n is zero or 1 have antibacterial activity. Among the compounds practically disclosed in the specification of the patent, however, the groups similar to those shown by the formula (1) or (3) as the group R in the compounds of this invention are only a pyridine-2-carbonyl group, a pyridine-3-carbonyl group, a 2,6-dioxo-4-piperidinyl-acetyl group, a 3-ethoxyquinoline-4-carbonyl group, and a 8-methoxyquinoline-2-carbonyl group; the groups similar to those shown by the formula (2) are only a 2-methylthio-5-bromopyrimidine-4-carbonyl group; and the groups similar to those shown by the formula (4) are a 2H-2-oxopyran-5-carbonyl group. Other examples of the group are an isoxazole carbonyl group, a furan carbonyl group, a thiophene carbonyl group, etc. The compounds of this invention are novel compounds which are not disclosed in the aforesaid patent.

It is described in the specification of the above-mentioned U.S. patent that the compounds disclosed in the patent show antibacterial activity to gram-positive and gram-negative bacteria but no practical numerical values for illustrating the activity are shown in the specification of the patent. Furthermore, although in the specification of Japanese Pat. No. 20986/'69 corresponding to the above-mentioned U.S. patent, the values of M. I. C. to the two varieties of Pseudomonas group which is a gram-negative bacterium are shown, the most potent value is only 125 γ/ml.

As results of investigating compounds having more potent antibacterial power than the compounds disclosed in the aforesaid U.S. patent and Japanese patent, the inventors have succeeded in discovering the compounds of this invention.

The compounds of the present invention show excellent antibacterial power to gram-positive and gram-negative bacteria and in particular they are effecttive against the bacteria belonging to the Pseudomonas group, which is a most important feature of this invention. It is known that when patients have a serious internal desease, in particular the aged and children having such desease are infected with the aforesaid bacterium, the treatment of the desease becomes quite difficult, frequently resulting in death of the patients and thus the discovery of medicaments effective against the aforesaid bacteria has been an urgent need.

The fact that the compounds of the present invention are very effect effective against the aforesaid bacteria as compared with the compounds disclosed in the indicated aforesaid U.S. patent and other known compounds will be shown below by the M. I. C. values.

| RCO | MIC (γ/ml) | | | | | MLD (g/Kg s.c.) DDN mice (male) |
| --- | --- | --- | --- | --- | --- | --- |
| | E. Coli Kauffmann 0-1 | Kleb. pneumoniae ATCC 10031 | Prot. vulgaris OXK US | Pseud. aeruginosa ATCC 8689 | Staph. aureus | |
| 1-methyl-4-oxoquinoline-3-carbonyl | ≥3 | ≥3 | 10 | 10 | 0.3 | 3 |
| 6-methyl-4-oxoquinoline-3-carbonyl (NH) | 3 | 1 | 3 | 10 | ≥0.3 | 1 |
| 1,6-dimethyl-4-oxoquinoline-3-carbonyl | 10 | 3 | 10 | 10 | ≥0.3 | 2 |
| 6-ethoxy-1-methyl-4-oxoquinoline-3-carbonyl | ≥10 | ≥3 | 10 | ≥10 | 1 | 1 |
| 1-ethyl-7-methylthio-4-oxoquinoline-3-carbonyl | ≥10 | ≥3 | 10 | ≥10 | ≥0.3 | 10 |
| 6-acetamido-4-oxoquinoline-3-carbonyl (NH) | 3 | ≥3 | 3 | 10 | 1 | <1 |
| 6-ethoxy-4-oxoquinoline-3-carbonyl (NH) | 3 | 1 | ≥3 | 10 | 1 | 2 |
| 7-methylthio-4-oxoquinoline-3-carbonyl (NH) | ≥0.3 | ≥0.3 | 0.1 | 10 | ≥0.1 | 7 |

-continued
| RCO | MIC (γ/ml) | | | | | MLD (g/Kg s.c.) DDN mice (male) |
|---|---|---|---|---|---|---|
| | E. Coli Kauffmann 0–1 | Kleb. pneumoniae ATCC 10031 | Prot. vulgaris OXK US | Pseud. aeruginosa ATCC 8689 | Staph. aureus | |
| 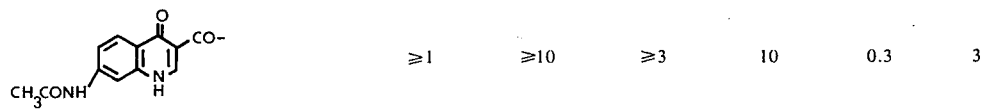 | ≥1 | ≥10 | ≥3 | 10 | 0.3 | 3 |
| 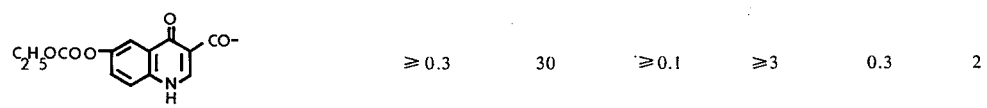 | ≥0.3 | 30 | ≥0.1 | ≥3 | 0.3 | 2 |
| 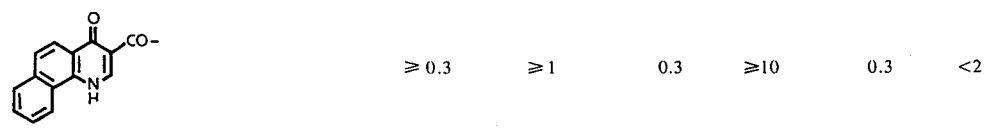 | ≥0.3 | ≥1 | 0.3 | ≥10 | 0.3 | <2 |
| 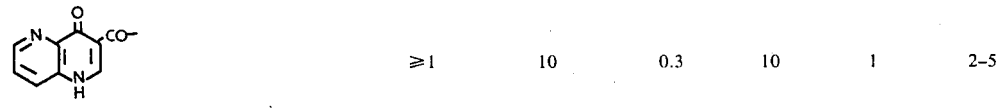 | ≥1 | 10 | 0.3 | 10 | 1 | 2–5 |
| 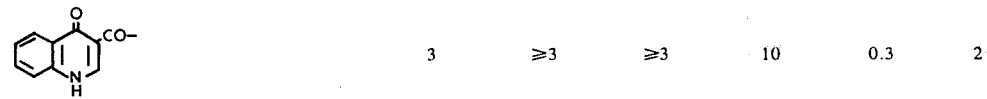 | 3 | ≥3 | ≥3 | 10 | 0.3 | 2 |
| 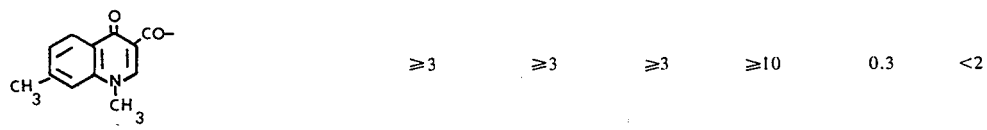 | ≥3 | ≥3 | ≥3 | ≥10 | 0.3 | <2 |
|  | 3 | 3 | 3 | ≥10 | 1 | 2 |
| 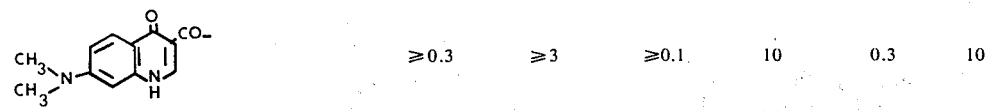 | ≥0.3 | ≥3 | ≥0.1 | 10 | 0.3 | 10 |
|  | ≥3 | 100 | ≥0.1 | 10 | 0.3 | 10 |
| 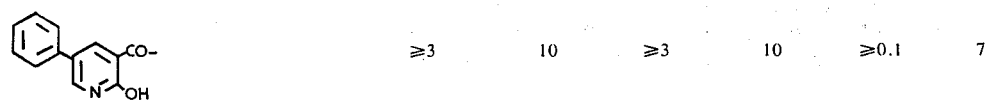 | ≥3 | 10 | ≥3 | 10 | ≥0.1 | 7 |

-continued

| RCO | MIC (γ/ml) | | | | | MLD (g/Kg s.c.) DDN mice (male) |
|---|---|---|---|---|---|---|
| | E. Coli Kauffmann 0-1 | Kleb. pneumoniae ATCC 10031 | Prot. vulgaris OXK US | Pseud. aeruginosa ATCC 8689 | Staph. aureus | |
| 4-hydroxypyridine-3-CO– | ≥3 | ≥30 | ≥3 | 3 | 0.3 | 10 |
| 2,4-dihydroxypyridine-3-CO– | 6 | >100 | ≥0.3 | 10 | 3 | 7 |
| 2,4-dioxo-tetrahydropyrimidine-5-CO– | ≥3 | 100 | ≥0.03 | 10 | 0.3 | 10 |
| 3-hydroxy-4-oxo-4H-pyran-6-CO– | ≥10 | ≥100 | ≥1 | ≥10 | 1 | 9 |
| pyridine-2-CO– | ≥10 | 30 | 1 | 30 | 0.3 | |
| phthalimidoacetyl (N-CH₂CO–) | ≥10 | 100 | — | 100 | 1 | |
| 2-oxo-2H-pyran-5-CO– | ≥10 | 100 | — | >100 | 0.3 | |
| pyridine-3-CO– | ≥10 | 100 | ≥1 | ≥30 | 0.3 | |
| Ampicillin | 3–10 | ≥30 | 3–10 | >100 | ≥0.03 | |
| Carbenicillin | ≥3 | >100 | 3 | 100 | 1 | |

The compounds of the present invention may be prepared by various methods. For example, the compounds of this invention may be prepared by reacting ampicillin and carboxylic acid represented by the formula

RCOOH wherein R has the same significance as mentioned above or a reactive derivative thereof. When the carboxylic acid is used in the reaction, it is preferable to use a condensing agent such as dicyclohexylcarbodiimide, carbonyldiimidazole, etc. Examples of the reactive derivatives of the carboxylic acid include an acid halide such as acid chloride, acid bromide, etc.; an acid anhydride; carboxy anhydride prepared by the reaction of RCOOH and an acid, for example an alkoxyhalocarbonic acid such as ethyl chlorocarbonate, ethyl bromocarbonate, etc; an aryloxyhalo carbonic acid or an arylthiohalocarbonic acid such as p-nitrophenyl chlorocarbonate, thiophenyl chlorocarbonate, etc.; a mixed acid anhydride prepared by the reaction of RCOOH and an acid such as alkyl phosphoric acid, dialkyl phosphorous acid, sulfuric acid, etc.; an active ester prepared by the reaction of RCOOH and p-nitrophenol, etc.; an acid azide; and the like.

Furthermore, the compounds of this invention may be prepared by reacting the carboxylic acid represented by the aforesaid formula RCOOH or the reactive derivative thereof and an ester of ampicillin that is, ampicillin in which the carboxyl group thereof has been protected by a protective group capable of releasing by a mild condition. Examples of the protective group for the carboxyl group capable of being released under mild conditions are a 2,2,2-trichloroethyl group, a bis(p-methoxyphenyl)methyl group, a benzhydryl group, a phenacyl group, a p-bromophenacyl group, a 3,5-di-tert-butyl-4-hydroxybenzyl group, etc. Those protective groups can be released from the carboxyl group by a known methods such as an alkali treatment, acid treatment and reductive release.

For example, when the carboxyl group has been protected by a group capable of being released therefrom by an alkali treatment, such as a phenacyl group, a p-bromophenacyl group, a 3,5-di-tert-butyl-4-hydroxybenzyl group, a p-methylsulfophenyl group, a dimethylaminoethyl group, etc., the protective group can be released by treating the compound in a solvent such as water, acetone, tetrahydrofuran, dimethylformamide, etc., or a mixture thereof of them with an inorganic or organic base such as sodium bicarbonate, sodium carbonate, sodium hydroxide, sodium hydride, sodium amide, sodium ethylate, sodium thiophenolate, cyclohexylamine, monoethylamine, diethylamine, potassium 2-ethylhexanoate, etc. Furthermore, when the carboxyl group has been protected by a group capable of being released by an acid treatment, such as a bis(p-methoxyphenyl)methyl group, a fluorenyl group, a phthalimidemethyl group, a trimethylsilyl group, tributyltin, etc., the protective group can be released by treating with hydrogen chloride, trifluoroacetic acid, sulfuric acid, phosphoric acid, etc. Moreover, when the carboxyl group has been protected by a group capable of being released by reduction, such as a 2,2,2-trichloroethyl group, a benzyl group, a p-nitrobenzyl group, etc., the protective group can be released by such treatment as catalytic reduction and chemical reduction. The conditions for the aforesaid treatment for releasing the protective group may be properly selected according to the property of the protective group.

Still further, the compounds of the present invention may be prepared by reacting 6-aminopenicillanic acid or a 6-aminopenicillanic acid derivative, i.e., aminopenicillanic acid in which the carboxyl group has been protected by a protective group capable of being released under mild conditions and the N-acylated phenyl glycine represented by the formula

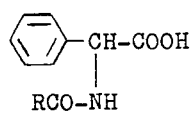

or a reactive derivative thereof prepared by the reaction of phenylglycine and the carboxylic acid represented by the formula RCOOH or a reactive derivative thereof and, if the reaction product has the protective group, releasing the protective group by a known method.

The invention will now be illustrated in and by the following examples.

EXAMPLE 1

In 20 ml. of dichloromethane was suspended 2.0 g. of ampicillin tri-hydrate and then after adding to the suspension 1 g. of anhydrous magnesium sulfate, 1.05 ml. of triethylamine was added to the mixture with stirring. After stirring the mixture for 20 minutes at room temperature, magnesium sulfate was filtered off. The magnesium sulfate thus separated was washed with 5 ml. of dichloromethane. The dichloromethane used for washing was combined with the filtrate recovered in the above step to provide a solution of ampicillin triethylamine salt.

Apart from this, 1.16 g. of 1-ethyl-7-methyl-4-oxo-1,4-dihydro-1,8-naphthylidine-3-carboxlic acid was dissolved in 30 ml. of dichloromethane and then 0.73 ml. of triethylamine was added to the solution. The solution was cooled to −20°C., 5 ml. of dichloromethane containing 0.5 ml. of ethyl chlorocarbonate was added dropwise to the solution with stirring, and the mixture was stirred for one hour at the same temperature.

Then to the solution was added dropwise the solution of the ampicillin triethylamine salt prepared in the aforesaid step at temperatures of −20°to −15°C. and after removing the cooling bath, the resultant mixture was stirred for 2.5 hours at room temperature. The reaction product was concentrated at a low temperature under a reduced pressure and the residue obtained was dissolved in 50 ml. of cold water. The aqueous solution was adjusted to pH 2 with 10% hydrochloric acid and the precipitates thus formed were extracted twice each with 20 ml. of ethyl acetate. The ethyl acetate extracts were combined with each other and washed three times each time with 10 ml. of saturated aqueous sodium chloride solution. After drying the ethyl acetate phase recovered over anhydrous magnesium sulfate, an n-butanol solution of 30% sodium 2-ethylhexanoate was added dropwise to it until no further deposition of white crystals formed.

The crystals thus formed were recovered by filtration, washed with ethyl acetate and then ether, and dried to provide 1.86 g. of the white powdery crystal of D-α-(1-ethyl-7-methyl-4-oxo-1,4-dihydro-1,8-naphthylidine-3-carbonylamino)benzylpenicillin sodium.

Yield 63.6%

Melting point 224–6°C. (decom.)

Infrared absorption spectrum: $\nu_{max}^{KBr}$ cm.$^{-1}$: 1760 (β-lactam), 1680–1640 broad (amide, ketone), 1600 (carboxylate, aromatic ring).

Nuclear magnetic resonance spectrum (D$_6$-DMSO): δ: 1.36(3H, $\underline{CH_3}$—CH$_2$—N<), 1.49 (6H,

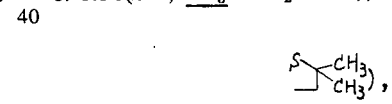

3.90 (1H,

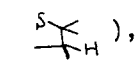

4.57 (2H, CH$_3$—$\underline{CH_2}$—N<), 5.36 (2H,

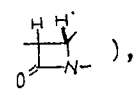

6.04 (1H,

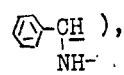

about 7,4 (6H, aromatic ring) 8.96 (1H,

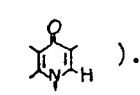

EXAMPLE 2

In 40 ml. of hexamethyl phosphor was suspended 1.02 g. of 1-methyl-4-quinoline-3-carboxylic acid and after adding 0.73 ml. of triethylamine to the suspension, the mixture was stirred for about 30 minutes. After cooling the suspension to 0°–5°C., 5 ml. of dichloromethane containing 0.5 ml. of ethyl chlorocarbonate was added dropwise to the suspension and the mixture was stirred for 1 hour at the same temperature as above. After adding to the reaction product the solution of ampicillin triethylamine salt prepared by using 2.0 g. of ampicillin tri-hydrate according to the method shown in Example 1 at 0°–3°C., the cooling bath was removed and the mixture was stirred for 3 hours at room temperature. The insoluble materials were filtered off and washed with 5 ml. of dichloromethane. The dichloromethane used for washing was combined with the filtrate and after adding thereto 30 ml. of dichloromethane and then 80 ml. of ice water, 10% hydrochloric acid was added dropwise to the mixture with stirring. The aqueous phase thus formed was adjusted to pH 2. After shaking sufficiently, the dichloromethane phase formed was separated and washed three times each time with 20 ml. of cold water. The product was dried over anhydrous magnesium sulfate and concentrated at a low temperature under a reduced pressure.

The remaining oily material thus obtained was dissolved in 30 ml. of ethyl acetate and while stirring the solution, an n-butanol solution of 30% sodium 2-ethylhexanoate was added thereto dropwise with stirring until no further deposition of white crystals formed.

The crystals were recovered by filtration, washed with ethyl acetate and then ether, and dried to provide 1.93 g. of D-α-(1-methyl-4-quinolone-3-carbonylamino)-benzylpenicillin sodium as the white powdery crystal.

Yield 70.0%

Melting point 230°–233°C. (decomposed)

Infrared absorption spectrum: $\nu_{max}^{KBr}$: 1760 (β-lactam), 1660 broad (amide, ketone), cm$^{-1}$ 1600 (carboxylate, aromatic ring).

Nuclear magnetic resonance spectrum (D$_6$-DMSO):δ: 1.50 (6H,

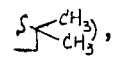), 3.54 (3H, CH$_3$—N<), 3.98 (1H,

), 5.40 (2H,

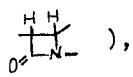), 6.06 (1H,

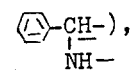), about 7.4 (6H, aromatic ring), 8.81 (1H,

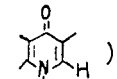)

EXAMPLES 3–20

The compounds of this invention were prepared by reacting ampicillin tri-hydrate and equimolar amounts of the dihydropyridine carboxylic acid derivatives according the method as shown in Example 2. The compounds obtained, the reactants, yields (%), and the melting points of the products are shown in the following table.

| Ex. No. | Product | Reagent | Yield (%) | Properties of product | Melting point (decomp.) (°C) |
|---|---|---|---|---|---|
| 3. | α-6-methyl-4-quinolone-3-carbonylamino)benzylpenicillin sodium | 6-methyl-4-quinolone-3-carboxylic acid | 60.0 | white powdery crystal | 220–224 |
| 4. | α-(1,6,7-trimethyl-4-quinolone-3-carbonylamino)benzylpenicillin postassium | 1,6,7-trimethyl-4-quinolone-3-carboxylic acid | 36.4 | yellow powdery crystal | 182–188 |
| 5. | α-(8-trifluoromethyl-4-quinolone-3-carbonylamino)benzylpenicillin sodium | 8-trifluoromethyl-4-quinolone-3-carboxylic acid | 40.7 | white powdery crystal | 206–210 |
| 6. | α-(7-trifluoromethyl-1-methyl-4-quinolone-3-carbonylamino)benzylpenicillin sodium | 7-trifluoromethyl-1-methyl-4-quinolone-3-carboxylic acid | 59.0 | white powdery crystal | 220–223 |
| 7. | α-(6-chloro-1-methyl-4-quinolone-3-carbonylamino)benzylpenicillin sodium | 6-chloro-1-methyl-4-quinolone-3-carboxylic acid | 62.0 | faint yellow powdery crystal | 238–242 |
| 8. | α-(8-chloro-1-methyl-4-quinolone-3-carbonylamino)benzylpenicillin sodium | 8-chloro-1-methyl-4-quinolone-3-carboxylic acid | 57.3 | white powdery crystal | 228–232 |
| 9. | α-(6,7-dichloro-1-methyl-4-quinolone-3-carbonylamino)benzylpenicillin sodium | 6,7-dichloro-1-methyl-4-quinolone-3-carboxylic acid | 45.6 | white powdery crystal | 247–254 |
| 10. | α-(1-ethyl-6-nitro-4-quinolone-3-carbonylamino)benzylpenicillin potassium | 1-ethyl-6-nitro-4-quinolone-3-carboxylic acid | 91.0 | yellow powdery crystal | 236–240 |
| 11. | α-(1-ethyl-7-nitro-4-quinolone-3-carbonylamino)benzylpenicillin potassium | 1-ethyl-7-nitro-4-quinolone-3-carboxylic acid | 91.3 | yellow powdery crystal | 260–268 |
| 12. | α-(1,6-dimethyl-4-quinolone-3-carbonylamino)benzylpenicillin sodium | 1,6-dimethyl-4-quinolone-3-carboxylic acid | 73.6 | white powdery crystal | 224–226 |
| 13. | α-(6-ethoxy-1-methyl-4-quinolone-3-carbonylamino)benzylpenicillin sodium | 6-ethoxy-1-methyl-4-quinolone-3-carboxylic acid | 65.0 | white powdery crystal | 215–218 |

| Ex. No. | Product | Reagent | Yield (%) | Properties of product | Melting point (decomp.) (°C) |
|---|---|---|---|---|---|
| 14. | α-(1-ethyl-6-methylthio-4-quinolone-3-carbonylamino)benzylpenicillin potassium | 1-ethyl-6-methylthio-4-quinolone-3-carboxylic acid | 83.3 | white powdery crystal | 223–228 |
| 15. | α-(1-ethyl-7-methylthio-4-quinolone-3-carbonylamino)benzylpenicillin potassium | 1-ethyl-7-methylthio-4-quinolone-3-carboxylic acid | 80.0 | white powdery crystal | 214–221 |
| 16. | α-(6-acetyl-4-quinolone-3-carbonylamino)benzylpenicillin sodium | 6-acetyl-4-quinolone-3-carboxylic acid | 56.5 | yellow powdery crystal | 215–220 |
| 17. | α-(6-acetylamino-4-quinolone-3-carbonylamino)benzylpenicillin sodium | 6-acetylamino-4-quinolone-3-carboxylic acid | 32.3 | faint yellow powdery crystal | 240–245 |
| 18. | α-(6-acetylamino-1-methyl-4-quinolone-3-carbonylamino)benzylpenicillin sodium | 6-acetylamino-1-methyl-4-quinolone-3-carboxylic acid | 87.5 | white powdery crystal | 220–224 |
| 19. | α-(ethyl-7-methylsulfonyl-4-quinolone-3-carbonylamino)benzylpenicillin potassium | 1-ethyl-7-methylsulfonyl-4-quinolone-3-carboxylic acid | 91.0 | white powdery crystal | 212–215 |
| 20. | α-(4-oxo-4H-pyrido[1,2-a]pyrimidine-3-carbonylamino)benzylpenicillin sodium | 4-oxo-4H-pyrido[1,2-a]pyrimidine-3-carboxylic acid | 62.4 | white powdery crystal | 215–218 |

EXAMPLE 21

In 40 ml. of hexamethylphosphoramide was suspended 1.09 g. of 1-ethyl-4-quinoline-3-carboxylic acid and then 0.73 ml. of triethylamine was added to the suspension. The solution thus prepared was cooled to 0°–5°C., 5 ml. of dichloromethane containing 0.5 ml. of ethyl chlorocaronate was added dropwise to the solution with stirring, and the mixture was stirred for 1 hour at the same temperature as above. After adding to the transparent reaction product thus obtained the solution of ampicillin triethylamine salt prepared by using 2.0 g. of ampicillin tri-hydrate according to the method shown in Example 1 at temperatures lower than 5°C., the cooling bath was removed and the mixture was stirred for 2 hours at room temperature.

After adding to the reaction product 30 ml. of dichloromethane and then 80 ml. of ice water, 10% hydrochloric acid was added to the mixture with stirring and the aqueous phase thus formed was adjusted to pH 2. After shaking the mixture sufficiently, the dichloromethane phase formed was recovered and washed three times each time with 20 ml. of cold water. The product was dried over anhydrous magnesium sulfate and concentrated at a low temperature under a reduced pressure.

The oily residue thus formed was dissolved in 30 ml. of ethyl acetate and then with stirring an n-butanol solution of 30% sodium 2-hexanoate was added dropwise to the solution until no deposition of white crystals were observed. Then, the crystals formed were recovered by filtration, washed with ethyl acetate and then ether, and dried to provide 1.90 g. of the white powdery crystal of D-α-(1-ethyl-4-quinoline-3-carbonylamino)benzylpenicillin sodium.

Yield: 67.2%

Melting point: 220°–222°C. (decomp.)

Infrared absorption spectrum: $\nu_{max}^{KBr}$ cm$^{-1}$: 1760 (β-lactam), 1660 broad (amide, ketone), 1600 (carboxylate, aromatic ring).

Nuclear magnetic resonance spectrum: (D$_6$-DMSO) δ: 1.36 (3H, $\underline{CH_3}$—CH$_2$—N<), 1.52 (6H,

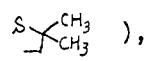 ), 3.98 (1H,

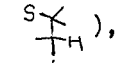 ), 4.51 (2H, CH$_3$—$\underline{CH_2}$—N<), 5.40 (2H,

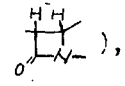 ), 6.08 (1H,

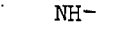 ), 7.35–7.65 (6H, aromatic ring H), 8.90 (1H,

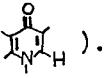 ).

EXAMPLE 22

To a suspension of 1.19 g. of 7-chloro-1-methyl-4-quinolone-3-carboxylic acid in 75 ml. of hexamethylphosphor amide was added 0.73 ml. of triethylamine and the mixture was stirred for about 30 minutes. The suspension was cooled to 0°–5°C., 5 ml. of dichloromethane containing 0.5 ml. of ethyl chlorocarbonate was added dropwise thereto with stirring, and the mixture was further stirred for 1 hour at the same temperature.

After adding dropwise to the reaction product the solution of ampicillin triethylamine salt prepared by using 2.0 g. of ampicillin tri-hydrate according to the method as shown in Example 1 at 0°–3°C., the cooling bath was removed and the mixture was stirred for 1 hour at room temperature.

The insoluble materials were filtered off and washed with 5 ml. of dichloromethane. The dichloromethane used for washing was combined with the filtrate obtained above and after adding thereto 50 ml. of dichloromethane and then 150 ml. of ice water, 10% hydrochloric acid was added dropwise to the mixture with stirring and the aqueous phase formed was adjusted to pH 2. After shaking sufficiently, the dichloromethane phase formed was recovered and washed three times each time with 30.0 ml. of cold water. The product was dried over anhydrous magnesium sulfate and concentrated at a low temperature under a reduced pressure. The oily residue was dissolved in 30 ml. of ethyl acetate and an n-butanol solution of 30% sodium 2-ethylhexanoate was added dropwise to the solution until no further deposition of white crystals formed.

The crystals thus formed were recovered by filtration, dried ethyl acetate and then ether, and dried to provide 1.6 g. of the white powdery crystal of D-α-(7-chloro-1-methyl-4-quinolone-3-carbonylamino)benzylpenicillin sodium.

Yield: 54.6%

Melting point: 240°–243°C. (decom.).

Infrared absorption spectrum: $\nu_{max}^{KBr}$ cm$^{-1}$: 1760 (β-lactam), 1640 broad (amide, ketone), 1595 (caarboxylate, aromatic ring).

Nuclear magnetic resonance spectrum: (D$_6$-DMSO + D$_2$O) δ: 1.43 (6H,

3.85 (3H, CH$_3$—N<), 4.00 (1H,

5.39 (2H,

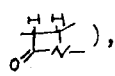

5.81 (1H,

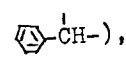

7.42 (5H,

7.76 (1H,

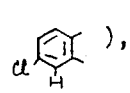

8.65

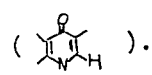

EXAMPLE 23

In a mixture of 25 ml. of hexamethylsphosphoramide and 25 ml. of dichloromethane was suspended 1.26 g. of 1-ethyl-7-chloro-4-quinolone-3-carboxylic acid and after adding to the suspension 0.73 ml. of triethylamine, the mixture was stirred for about 30 minutes.

The suspension was cooled to 0°–5°C., and after adding dropwise to the suspension 5 ml. of dichloromethane containing 0.5 ml. of ethyl chlorocarbonate with stirring, the mixture was stirred for 1 hour at the same temperature.

After adding dropwise to the reaction product thus obtained the solution of ampicillin triethylamine salt prepared by using 2.0 g. of ampicillin tri-hydrate according to the method shown in Example 1 at 0°–3°C., the cooling bath was removed and the mixture was further stirred for 3 hours at room temperature. The insoluble materials were filtered off and washed with 5 ml. of dichloromethane. The dichloromethane used for washing was combined with the filtrate obtained above and after adding thereto 30 ml. of dichloromethane and then 50 ml. of ice water, 10% hydrochloric acid was added dropwise to the solution with stirring, the aqueous phase formed was adjusted to pH 2. After shaking sufficiently, the dichloromethane phase thus formed was recovered and washed three times each time with 20 ml. of cold water. The product was dried over anhydrous magnesium sulfate and then concentrated at a low temperature under a reduced pressure. The oily residue was dissolved in 30 ml. of ethyl acetate and then an n-butanol solution of 30% sodium 2-ethylhexanoate was added dropwise to the solution until no further deposition of white crystals formed.

The crystals thus formed were recovered by filtration, washed with ethyl acetate and then ether, and dried to provide 1.85 g. of the white powdery crystal of D-α-(1-ethyl-7-chloro-4-quinolone-3-carbonylamino)-benzylpenicillin sodium.

Yield: 61.7%

Melting point: 235°–242°C. (decom.).

Infrared abosrption spectrum: $\nu_{max}^{KBr}$ cm.$^{-1}$: 1765 (β-lactam), 1655 broad (amide, ketone), 1600 (carboxylate, aromatic ring).

Nuclear magnetic resonance spectrum (D$_6$-DMSO): ppm.: 1.38 (3H, CH$_3$—CH$_2$—N<), 1.45 (6H,

3.90 (1H,

4.44 (2H, CH$_3$—CH$_2$—N<), 5.35 (2H,

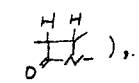

5.98 (1H,

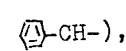

7.35 (5H,

8.00

(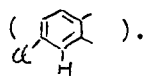), 8.84 (1H, (1H, 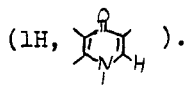).

EXAMPLE 24

To a suspension of 1.28 g. of 7-trifluoromethyl-4-quinolone-3-carboxylic acid in 80 ml. of dichloromethane was added 0.73 ml. of triethylamine and after cooling the solution to temperatures of −20° to −10°C., 5 ml. of dichloromethane containing 0.5 ml. of ethyl chlorocarbonate was added dropwise to the solution with stirring, the mixture was stirred for 1.5 hours at the same temperature. After adding dropwise to the reaction product the solution of ampicillin triethylamine salt prepared by using 2.0 g. of ampicillin tri-hydrate according to the method shown in Example 1 at −20° to −15°C., the cooling bath was removed and the mixture was stirred for 2.5 hours at room temperature.

By treating the reaction product by the manner as in Example 1, 1.32 g. of the white powdery crystal of D-α-(7-trifluoromethyl-4-quinolone-3-carbonylamino)benzylpenicillin sodium was obtained.

Yield: 43.6%

Melting point: 245°–250°C. (decomposed).

Infrared absorption spectrum: $\nu_{max}^{KBr}$ cm.$^{-1}$: 1765 (β-lactam), 1740–1750 broad (amide, ketone), 1605 (carboxylate, aromatic ring).

EXAMPLE 25

To a suspension of 1.16 g. of 6-ethoxy-4-quinolone-3-carboxylic acid in 25 ml. of hexamethyl phosphor amide was added 0.73 ml. of triethylamine and the mixture was stirred for about 30 minutes. The suspension was cooled to 0–5°C., 5 ml. of dichloromethane containing 0.5 ml. of ethyl chlorocarbonate was added dropwise to the suspension with stirring and the mixture was stirred for 1 hour at the same temperature.

After adding dropwise to the reaction product the solution of ampicillin triethylamine salt prepared by using 2.0 g. of ampicillin tri-hydrate according to the method shown in Example 1 at 0°–3°C., the cooling bath was removed and the mixture was stirred for 1 hour at room temperature. By treating the reaction product by the same manner as in Example 5, 1.50 g. of the white powdery crystals of D-α-(6-ethoxy-4-quinolone-3-carbonylamino)benzylpenicillin sodium was obtained.

Yield 51.6%

Melting point: 205°–211°C. (decomposed).

Infrared absorption spectrum: $\nu_{max}^{KBr}$ cm.$^{-1}$: 1765 (β-lactam), 1670–1640 broad (amide, ketome), 1605 (carboxylate, aromatic ring).

EXAMPLE 26

In 7 ml. of dichloromethane was suspended 403 mg of ampicillin tri-hydrate and 200 mg. of anhydrous magnesium sulfate and then 0.21 ml. of triethylamine was added to the suspension. After stirring the mixture for 20 minutes at room temperature, magnesium sulfate was fitlered off. The magnesium sulfate thus filtered was washed with a small amount of dichloromethane and the dichloromethane used for washing was combined with the filtrate to provide ampicillin triethylamine solution.

In a mixture of 6 ml. of hexamethyl phosphor amide, 4 ml. of dichloromethane, and 10 ml. of dioxane was suspended 260 mg. of 6-methyl-6,9-dihydro-9-oxoisothiazolo[4,3-f]quinoline-8-carobxylic acid and after adding thereto 0.14 ml. of triethylamine, the mixture was stirred for about 1 hour.

The suspension was cooled to 0°–5°C. and after adding dropwise to the suspension 2 ml. of dichloromethane contaning 0.1 ml. of ethyl chlorocarbonate with stirring, the mixture was stirred for 1 hour at the same temperature. Then, after adding dropwise to the reaction product the solution ampicilline triethylamine salt prepared above at 0°–5°C., the cooling bath was removed and the mixture was stirred for 2 hours at room temperature. After adding thereto 30 ml. of dichloromethane, the insoluble materials were filtered off and washed with a small amount of dichloromethane. The dichloromethane used for washing was combined with the filtrate and after adding thereto 30 ml. of ice water, 10% hydrochloric acid was added dropwise to the mixture with stirring and the aqueous phase thus formed was adjusted to pH 2.

After shaking the mixture sufficiently, the dichloromethane phase thus formed was recovered and washed three times each time with 10 ml. of cold water. The product was dried over anhydrous magnesium sulfate and concentrated at a low temperature under a reduced pressure. The residue was dissolved in 10 ml. of ethyl acetate and an n-butanol solution of 30% sodium 2-ethylhexanoate was added to the solution until no further deposition of white crystals occured.

The crystals were recovered by filtration, washed with ethyl acetate and then ether, and dried to provide 280 mg. of the white powdery crystal of D-α-(6-methyl-6,9-dihydro-9-oxoisothiazolo[4,3-f]quinoline-8-carbonylamino)benzylpenicillin sodium.

Yield: 45.6%

Melting point 235°–242°C. (decomp.)

Infrared absorption spectrum: $\nu_{max}^{KBr}$ Cm.$^{-1}$: 1770 (β-lactam), 1660 broad (amide, ketone), 1600 broad (carboxylate, aromatic ring).

Nuclear magnetic resonance spectrum (D$_6$-DMSO+D$_2$O): δ: 1.48 (6H,

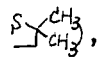, 4.03 (1H,

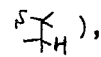, 5.42 (2H,

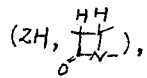, 5.98 (1H,

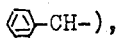), about 7.45 (6H, aromatic ring H), 8.60 (1H,

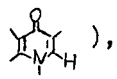), 10.54 (1H,

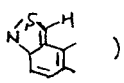 )

EXAMPLE 27

In 10 ml. of hexamethyl phosphor amide was suspended 260 mg. of 6-methyl-6,9-dihydro-9-oxo-thiazolo[5,4-f]quinoline-8-carboxylic acid and after adding thereto 0.14 ml. of triethylamine, the mixture was stirred for about 1 hour.

The suspension was cooled to 0°–5°C. and after adding dropwise to the suspension 2 ml. of dichloromethane containing 0.1 ml. of ethyl chlorocarbonate with stirring, the mixture was stirred for 1 hour at the same temperature. Then, after adding dropwise to the reaction product the solution of ampicillin triethylamine salt by using 403 mg. of ampicillin tri-hydrate according to the method shown in Example 26 at 0°–5°C., the cooling bath was removed and the mixture was stirred for 2 hours at room temperature. After adding thereto 30 ml. of dichloromethane, the insoluble materials were separated by filtration and washed with a small amount of dichloromethane. The dichloromethane used for washing was combined with the filtrate and after adding thereto 30 ml. of ice water, 10% hydrochloric acid was added dropwise to the mixture with stirring and the aqueous phase thus formed was adjusted to pH 2. After filtering off a small amount of the precipitates, the dichloromethane phase obtained was recovered and washed three times each time with 10 ml. of cold water. The product was dried over anhydrous magnesium sulfate and concentrated at a low temperature under a reduced pressure. The residue was dissolved in 10 ml. of ethyl acetate and then an n-butanol solution of 30% sodium 2-ethylhexanoate was added dropwise to the solution until no further deposition of white crystals formed.

The crystals thus formed were reovered by filtration, washed with ethyl acetate and then ether, and dried to provide 263 mg. of the white powdery crystal of D-α-(6-methyl-6,9-dihydro-9-oxothiazolo[5,4-f]quinoline-8-carbonylamino)benzylpenicillin sodium.

Yield 42.9%

Melting point: 258°–260°C. (decomp.).

Infrared absorption spectrum: $\nu_{max}^{KBr}$ cm.$^{-1}$: 1765 (β-lactam), 1655 broad (amide, ketone), 1610–1600 (carboxylate, aromatic ring).

Nuclear magnetic resonance spectrum (D$_6$-DMSO): ppm.: 1.52 (6H,

, 4.02 (1H,

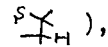), 4.19 (3H, CH$_3$—N<) 5.42 (2H,

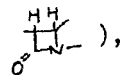), 6.09 (1H,

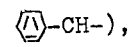), about 7.40 (6H, aromatic ring H), 8.90 (1H,

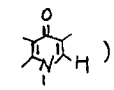 )

EXAMPLE 28

In 20 ml. of 50% alcohol was suspended 300 mg. of 6-ethyl-3-methyl-2,9-dioxo-2,3,6,9-tetrahydro-thiazolo[5,4-f]quinoline-8-carboxylic acid and after adding 0.6 ml. of triethylamine to the suspension, the mixture was concentrated under a reduced pressure to provide a white powdery triethylamine salt.

After suspensing the triethylamine salt thus obtained in 15 ml. of hexamethyl phosphor amide and further adding dropwise to the suspension 0.2 ml. of triethylamine, the mixture was cooled to 0°–5°C., 2 ml. of dichloromethane containing 0.1 ml. of ethyl chlorocarbonate was added dropwise, the mixture was stirred for 2 hours at the same temperature.

Then, after adding dropwise to the reaction product the solution of ampicillin triethylamine salt prepared by using 403 mg. of ampicillin tri-hydrate according to the method shown in Example 26 at 0°–5°C., the cooling bath was removed and the mixture was stirred for 2 hours at room temperature. After adding 30 ml. of dichloromethane to the product, the insoluble materials were separated by filtration and the filtrate was treated by the same method as in Example 26 to provide 145 mg. of the white powdery crystal of D-α-(6-ethyl-2,3,6,9-tetrahydro-3-methyl-2,9-dioxo-thiazolo[5,4-f]-quinoline-8-carbonylamino)benzyl-penicillin sodium.

Yield 22.0 %

Melting point: 247°–249°C. (decomp.)

Infrared absorption spectrum: $\nu_{max}^{KBr}$ cm.$^{-1}$: 1765 (β-lactam), 1650 broad (amide, ketone), 1600 (carboxylate, aromatic ring).

Nuclear magnetic resonance spectrum: (D$_6$—DMSO) δ.: 1.23 (3H, CH$_3$—CH$_2$—N<), about 7.4 (6H, aromatic ring H), 1.48 (6H,

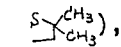, 3.90 (1H,

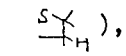), 8.85 (1H, 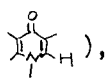), 4.48 (2H, CH$_3$—C$\underline{H}_2$—N<), 5.35 (2H, 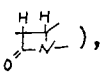), 6.03 (1H, 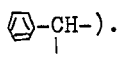).

EXAMPLES 29–47

The compounds of this invention were prepared by reacting ampicillin tri-hydrate and equimolar amount of dihydropyridine carboxylic acid derivatives by the same method as in Example 2.

The compounds thus obtained, the reactants used in the reaction, the yields (%) and the melting points of the products are shown in the following table.

EXAMPLE 48

In 100 ml. of dichloromethane was suspended 10 g. of ampicillin tri-hydrate and after adding to the suspension 3 g. of anhydrous magnesium sulfate, 8.75 ml. of triethylamine was added to the mixture with stirring. After stirring the mixture for 5 minutes at room temperature, magnesium sulfate was separated by filtration and washed with 5 ml. of dichloromethane. The dichloromethane thus used was combined with the filtrate obtained above to provide a solution of ampicillin triethylamine salt.

The solution was cooled to −20°C. and then 7.7 g. of 7-dimethylamino-4-quinolone-3-carboxylic acid chloride and 10 ml. of dichloromethane solution of 3.5 ml. of triethylamine were added alternately to the solution at −20° to −25°C. over a period of 30 minutes. Thereafter, the reaction product was stirred for 1 hour at the same temperature and concentrated at a low temperature under a reduced pressure.

The residue was dissolved in 100 ml. of ice water and after adding to the solution 100 ml. of n-butanol and 100 ml. of ethyl acetate and further adding dropwise thereto 6 N hydrochloric acid with stirring, the aqueous phase formed was adjusted to pH 3. The organic phase was recovered and washed twice each time with 50 ml. of cold water. Then, after drying the organic phase over anhydrous magnesium sulfate, 8 ml. of n-butanol solution of potassium 2-ethylhexanoate (i.e., containing 25 mM of potassium 2-ethylhexanoate per 1 ml.) was

| Example No. | Product | Reagent | Yield (%) | Properties of product | Melting point (decomp.) (°C) |
|---|---|---|---|---|---|
| 29. | α-(7-methyl-4-quinolone-3-carbonylamino)benzylpenicillin sodium | 7-methyl-4-quinolone-3-carboxylic acid | 59.7 | white powdery crystal | 219–230 |
| 30. | α-(7-acetyl-4-quinolone-3-carbonylamino)benzylpenicillin sodium | 7-acetyl-4-quinolone-3-carboxylic acid | 68.0 | white powdery crystal | 210–217 |
| 31. | α-(7-nitro-4-quinolone-3-carbonylamino)benzylpenicillin potassium | 7-nitro-4-quinolone-3-carboxylic acid | 74.5 | brown powdery crystal | 270–277 |
| 32. | α-(7-methylthio-4-quinolone-3-carbonylamino)benzylpenicillin potassium | 7-methylthio-4-quinolone-3-carboxylic acid | 66.6 | white powdery crystal | 245–248 |
| 33. | α-(7-acetylamino-4-quinolone-3-carbonylamino)benzylpenicillin sodium | 7-acetylamino-4-quinolone-3-carboxylic acid | 41.0 | faint yellow powdery crystal | 256–260 |
| 34. | α-(6-ethoxycarbonyloxy-4-quinolone-3-carbonylamino)benzylpenicillin sodium | 6-ethoxycarbonyloxy-4-quinolone-3-carboxylic acid | 76.3 | white powdery crystal | 218–223 |
| 35. | α-(6,7-dichloro-4-quinolone-3-carbonylamino)benzylpenicillin sodium | 6,7-dichloro-4-quinolone-3-carboxylic acid | 73.5 | faint yellow powdery crystal | 237–250 |
| 36. | α-(1-oxo-2,4-dihydrobenzo[f]quinoline-2-carbonylamino)benzylpenicillin sodium | 1-oxo-1,4-dihydrobenzo[f]quinoline-2-carboxylic acid | 67.4 | white powdery crystal | 236–242 |
| 37. | α-(4-oxo-1,4-dihydrobenzo[h]quinoline-3-carbonylamino)benzylpenicillin potassium | 4-oxo-1,4-dihydrobenzo[h]quinoline-3-carboxylic acid | 63.5 | white powdery crystal | 243–247 |
| 38. | α-(1-acetyl-8-oxo-2,3,5,8-tetrahydropyrrolo[2,3-g]quinoline-7-carbonylamino)benzylpenicillin sodium | 1-acetyl-8-oxo-2,3,5,8-tetrahydropyrrolo[2,3-g]quinoline-7-carboxylic acid | 62.4 | yellow powdery crystal | 258–263 |
| 39. | α-(6-ethyl-9-oxo-6,9-dihydrofuro[3,2-f]quinoline-8-carbonylamino)benzylpenicillin sodium | 6-ethyl-9-oxo-dihydrofuro[3,2-f]quinoline-8-carboxylic acid | 43.6 | yellow powdery crystal | 235–238 |
| 40. | α-(4-oxo-1,4-dihydro-1,5-naphthyridine-3-carbonylamino)benzylpencillin potassium | 4-oxo-1,4-dihydro-1,5-naphthyridine-3-carboxylic acid | 55.2 | brown powdery crystal | 237–243 |
| 41. | α-(4-oxo-1,4-dihydro-1,6-naphthyridine-3-carbonylamino)benzylpenicillin potassium | 4-oxo-1,4-dihydro-1,6-naphthyridine-3-carboxylic acid | 59.1 | white powdery crystal | 211–218 |
| 42. | α-(4-oxo-1,4-dihydro-1,7-naphthyridine-3-carbonylamino)benzylpenicillin potassium | 4-oxo-1,4-dihydro-1,7-naphthyridine-3-carboxylic acid | 52.0 | faint yellowish brown powdery crystal | 219–225 |
| 43. | α-(4-quinolone-3-carbonylamino)-benzylpenicillin sodium | 4-quinolone-3-carboxylic acid | 67.0 | white powdery crystal | 221–226 |
| 44. | α-(1,7-dimethyl-4-quinolone-3-carbonylamino)benzylpenicillin sodium | 1,7-dimethyl-4-quinolone-3-carboxylic acid | 52.4 | white powdery crystal | 236–242 |
| 45. | α-(1-methyl-6-methoxy-4-quinolone-3-carbonylamino)benzylpenicillin sodium | 1-methyl-6-methoxy-4-quinolone-3-carboxylic acid | 54.3 | brown powdery crystal | 220–223 |
| 46. | α-(6-methoxy-4-quinolone-3-carbonylamino)-benzylpenicillin sodium | 6-methoxy-4-quinolone-3-carboxylic acid | 58.2 | white powdery crystal | 225–229 |
| 47. | α-(7-methoxy-4-quinolone-3-carbonylamino)benzylpenicillin sodium | 7-methoxy-4-quinolone-3-carboxylic acid | 52.6 | white powdery crystal | 210–217 | added thereto and the crystals formed were recovered by filtration. The crystals thus obtained were washed with ethyl acetate and then ether and dried to provide 10.5 g. of the light-yellow powdery crystal of D-α-(7-dimethylamino-4-quinolone-3-carbonylamino)benzylpenicillin potassium.

Yield 70.3%

Melting point: 244°–249°C. (decomp.).

Infrared absorption spectrum: $\nu_{max}^{KBr}$ cm.$^{-1}$: 1760 (β-lactam), 1660 broad (amide, ketone), 1600 (carboxylate).

EXAMPLE 49

After stirring a mixture of 13.8 g. of ampicillin trihydrate, 10.2 g. of anhydrous magnesium sulfate, 7.15 ml. of triethylamine, and 240 ml. of dichloromethane for 1 hour at room temperature, magnesium sulfate was filtered off to provide dichloromethane solution of ampicillin triethylamine salt.

In 100 ml. of hexametapol was dissolved 5.2 g. of N-methyl-2-pyridone-3-carboxylic acid and then 4.76 ml. of triethylamine was added to the solution. Then, after adding dropwise to the solution 50 ml. of dichloromethane solution containing 3.06 ml. of ethyl chlorocarbonate at 0°–5°C., the mixture was stirred for 40 minutes at the same temperature. Then, the dichloromethane solution of ampicillin triethylamine salt prepared in the aforesaid step was added dropwise to the solution at 0°–5°C., the mixture was stirred for 3 hours at room temperature.

After adding to the reaction product 200 ml. of dichloromethane and 200 ml. of ice water and acidifying the mixture with dilute hydrochloric acid, the dichloromethane phase thus formed was recovered. The dichloromethane phase thus obtained was washed three times with water, dried over anhydrous magnesium sulfate and then the solvent was distilled away under a reduced pressure. The residue was dissolved in 150 ml. of ethyl acetate and then a butanol solution of 30% sodium ethylhexanoate was added to the solution, whereby a precipitate was formed. The precipitate was recovered by filtration and reprecipitated from methanol-ether to provide 4.4 g. of the white powder of α-(N-methyl-2-pyridone-3-carbonylamino)benzylpenicillin sodium.

Melting point: 201°–208°C. (decomp.)

Infrared absorption spectrum: $\nu_{max}^{KBr}$ Cm.$^{-1}$: 3440 (NH, OH), 1765 (β-lactam), 1655 (amide, ketone), 1600 (carboxylate).

Nuclear magnetic resonance spectrum (D$_6$-DMSO + H$_2$O): δ: 1.45, 1.56 (6H,

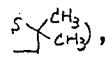), 3.68(3H,

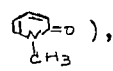), 4.08 (1H, s,

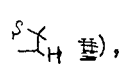), 5.50 (2H, q, 5.92 (1H, s,

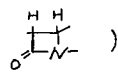), 6.68 (1H, t,

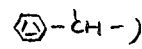), 7.52 (5H,

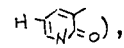), 8.10 (1H, q,

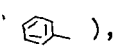), 8.50 (1H, q,

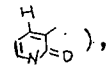).

EXAMPLE 50

After stirring a mixture of 806 mg. of ampicillin trihydrate, 600 mg. of magnesium sulfate, 0.42 ml. of triethylamine, and 14 ml. of dichloromethane for 1 hour at room temperature, the magnesium sulfate was filtered away to form a dichloromethane solution of ampicillin triethylamine salt.

To a solution prepared by adding 0.28 ml. of triethylamine to 5 ml. of a hexametapol solution containing 278 mg. of 2-hydroxynicotinic acid was added dropwise 5 ml. of a dichloromethane solution of 0.18 ml. of ethyl chlorocarbonate at 0°–5°C. and the mixture was stirred for 1 hour at the same temperature.

To the solution was added dropwise the dichloroethane solution of ampipicillin triethylamine salt prepared in the abovementioned step at 0°–5°C. and the mixture was stirred for 3 hours at room temperature. By treating the mixture as in Example 49 and re-precipitating from methanol-ether, 450 mg. of the white powder of α-(2hydroxynicotinoylamino)benzylpencillin sodium was obtained.

Melting point: 217°–223°C. (decomp.).

Infrared absorption spectrum: $\nu_{max}^{KBr}$ cm.$^{-1}$: 3430 (OH, NH), 1765 (β-lactam), 1660 (amide, ketone), 1600 (carboxylate).

Nuclear magnetic resonance spectrum (D$_6$-DMSO+D$_2$O): δ: 1.45 1.56 (6H,

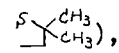), 4.08 (1H, s,

5.50 (2H, q,

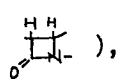

5.94 (1H, s,

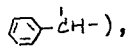

7.52 (6H,

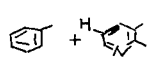

), 8.05 (1H, q,

8.60 (1H,

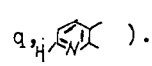

EXAMPLE 51

To 14 ml. of dichloromethane were added 806 mg. of ampicillin trihydrate, 600 mg. of magnesium sulfate, and 0.42 ml. of triethylamine and after stirring the mixture for about 1 hour at room temperature, magnesium sulfate was filtered off to provide a dichloromethane solution of ampicillin triethylamine salt.

In 20 ml. of hexametapol was suspended 278 mg. of 4-hydroxypicolinic acid and after adding 0.28 ml. of triethylamine to the suspension, the mixture was stirred for 30 minutes at room temperature. The transparent solution thus obtained was cooled to 0°–5°C. by ice water, 5 ml. of a dichloromethane solution containing 0.18 ml. of ethyl chlorocarbonate was added dropwise to the solution, and the mixture was stirred for one hour at the same temperature.

To the solution thus prepared was added dropwise the dichloromethane solution of ampicillin triethylamine salt prepared in the abovementioned step at 0°–5°C., and the mixture was stirred for 3 hours at room temperature. By treating the reaction product as in Example 49 and re-precipitating from methanol-ether, 200 mg. of a light-yellow powder of α-(4-hydroxypicolinoylamino)benzylpenicillin sodium was obtained.

Melting point: 227°–230°C. (decomposed)

Infrared absorption spectrum: $\nu_{max}^{KBr}$ cm.$^{-1}$: 3430 (NH, OH), 1765 (β-lactam), 1660 (amide, ketone), 1600 (carboxylate).

Nuclear magnetic resonance spectrum (D$_6$-DMSO+D$_2$O): δ: 1.42, 1.52 (6H,

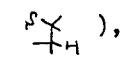

4.00 (1H, s,

5.42 (2H, q, 5.80 (1H, s, 6.65 (1H, q,

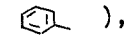

7.11 (1H, d, 7.40 (5H, 8.06 (1H, d,

EXAMPLE 52

After stirring a mixture of 806 mg. of ampicillin trihydrate, 600 mg. of magnesium sulfate, 0.42 ml. of triethylamine, and 14 ml. of dichloromethane for 1 hour at room temperature, magnesium sulfate was fitered off to provide a dichloromethane solution of ampicillin triethylamine salt.

In 15 ml. of hexametapol was dissolved 278 mg. of 6-hydroxypicolinic acid and after adding 0.28 ml. of triethylamine to the solution, the mixture was cooled to 0°–5°C. Then, to the mixture was added 5 ml. of a dichloromethane solution containing 0.18 ml. of ethylchlorocarbonate and the resultant mixture was stirred for 1 hour at the same temperature. To the solution was added dropwise the dichloromethane solution of ampicillin triethylamine salt prepared in the above-mentioned step at 0°–5°C. and the mixture was stirred for 3 hours at room temperature.

By treating the reaction mixture as in Example 49 and then re-precipitating from methanol-ether, 600 mg. of the light-yellow powder of α-(6-hydroxypicolinoylamino)benzylpenicillin sodium was obtained.

Melting point: 225°–228°C. (decomp.).

Infrared absorption spectrum: $\nu_{max}^{KBr}$ cm.$^{-1}$: 3430 (NH,OH), 1765 (β-lactam), 1640 (amide, ketone), 1595 (carboxylate).

Nuclear magnetic resonance spectrum (D$_6$-DMSO+D$_2$O): δ: 1.44, 1.55 (6H,

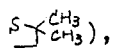), 5.43 (2H, q,

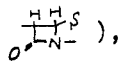), 5.90 (1H, s,

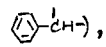), 6.65 (1H, q,

), 7.15 (1H, q,

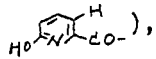), 7.44 (6H,

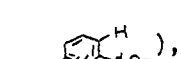).

EXAMPLE 53

After stirring a mixture of 1.45 g. of ampicillin trihydrate, 1.1 g. of magnesium sulfate, 1.0 ml. of triethylamine, and 20 ml. of dichloromethane for 1 hour at room temperature, magnesium sulfate was filtered off to provide a dichloromethane solution of ampicillin triethylamine salt.

In a mixture of 5 ml. of hexametapol and 5 ml. of dichloromethane was dissolved 500 mg. of 5-hydroxypicolinic acid and then after adding to the solution 0.52 ml. of triethylamine, the mixture was cooled to 0°–5°C. To the solution was added 0.34 ml. of ethyl chlorocarbonate, and the mixture was stirred for 30 minutes at the same temperature.

To the solution thus prepared was added dropwise at 0°–5°C. the dichloromethane solution of ampicillin triethylamine salt prepared in the above step and after stirring the mixture for 3 hours at room temperature, the mixture was allowed to stand overnight. By treating the reaction mixture as in Example 49 and reprecipitating from methanol-ether, 320 mg. of the light-yellow powder of α-(5-hydroxypicolinoylamino)-benzylpenicillin sodium was obtained.

Melting point: 205°–210°C. (decomp.).

Infrared absorption spectrum: $\nu_{max}^{KBr}$ cm.$^{-1}$: 3400 (NH, OH), 1760 (β-lactam), 1650 (amide, ketone), 1600 (carboxylate).

Nuclear magnetic resonance spectrum (D$_6$-DMSO+D$_2$O): δ: 1,46, 1.55 (6H,

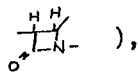), 5.44 (2H, q,

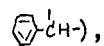), 5.95 (1H, s,

), 7.41 (5H,

), 7.80 (3H, m,

).

After stirring a mixture of 2.0 g. of ampicillin trihydrate, 1.5 g. of magnesium sulfate, 1.05 ml. of triethylamine, and 30 ml. of dichloromethane for 1 hour at room temperature, magnesium sulfate was filtered off to provide a dichloromethane solution of ampicillin triethylamine salt.

In a mixture of 25 ml. of dichloromethane and 10 ml. of hexametapol was dissolved 697 mg. of 6-hydroxynicotinic acid and after adding to the solution 0.72 ml. of triethylamine, the mixture was cooled to −10°C. Then, 0.48 ml. of ethyl chlorocarbonate was added dropwise to the solution, and the mixture was stirred for 1,5 hours at −10°C.

To the solution thus prepared was added the dichloromethane solution of ampicillin triethylamine salt prepared in the above step and after stirring the mixture for 1 hour at −10°C., the mixture was allowed to stand overnight at 2°C. After adding to the reaction mixture a saturated aqueous sodium chloride solution, the mixture was acidified with hydrochloric acid. The dichloromethane phase thus formed was recovered, washed three times with water, dried over magnesium sulfate, and the solvent was distilled off under a reduced pressure. The residue was dissolved in ethyl acetate and a butanol solution of 30% sodium 2-ethylhexanoate was added to the solution, whereby a precipitate were formed. By recovering the precipitate by filtration, 1.0 g. of the white powder of α-(6-hydroxynicotinoylamino)benzylpenicillin sodium was obtained.

Melting point: 229°–235°C. (decomp.).

Infrared absorption spectrum: $\nu_{max}^{KBr}$ cm.$^{-1}$: 3400 (NH, OH), 1760 (β-lactam), 1650 (amide, ketone), 1600 (carboxylate).

Nuclear magnetic resonance spectrum: (D$_6$-DNSO+D$_2$O) δ: 1.42, 1.50 (6H,

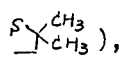

4.00 (1H, s,

5.40 (2H,

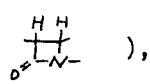

5.80 (1H, s,

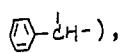

6.48 (1H, d,

7.40 (5H,

8.00 (1H, q,

8.16 (1H, d,

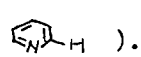).

EXAMPLE 55

After stirring a mixture of 930 mg. of ampicillin trihydrate, 0.5 ml. of triethylamine, 700 mg. of magnesium sulfate, and 20 ml. of dichloromethane for one hour at room temperature, magnesium sulfate was filtered off to provide a dichloromethane solution of ampicillin triethylamine salt.

In a mixture of 5 ml. of hexametapol and 5 ml. of dichloromethane was dissolved 320 mg. of 2-hydroxyisonicotinic acid and after adding to the solution 0.32 ml. of triethylamine, the mixture was cooled to 0°–5°C. After adding further to the solution 0.22 ml. of ethyl chlorocarbonate, the mixture was stirred for 1 hour.

To the solution prepared was added dropwise the dichloromethane solution of ampicillin triethylamine salt at 0°–5°C. and the mixture was stirred for 3 hours at room temperature. Then by treating the reaction mixture as in Example 49 and re-precipitating from methanol-ether, 210 mg. of a white powder of α-(2-hydroxyisonicotinoylamino)benzylpenicillin sodium was obtained.

Melting point: 205°–210°C. (decomp.)

Infrared absorption spectrum: $v_{max}^{KBr}$ cm.$^{-1}$: 3350 (NH, OH), 1770 (β-lactam), 1650 (amide, ketone), 1610 (carboxylate).

Nuclear magnetic resonance spectrum (D$_6$-DMSO+D$_2$O): δ: 1.47, 1.52 (6H,

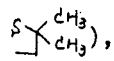

4.16 (1H, s,

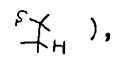

5.56 (2H, q,

5.89 (1H, s,

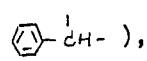

6.88 (1H, q,

7.08 (1H, d,

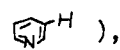

7.61 (6H,

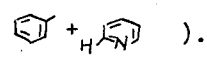).

EXAMPLE 56

In 60 ml. of dichloromethane was suspended 4.03 g. of ampicillin trihydrate and after adding to the solution 2.1 ml. of triethylamine and 4.0 g. of magnesium sulfate, the mixture was stirred for 30 minutes at room temperature. Then, by filtering off the magnesium sulfate, a dichloromethane solution of ampicillin triethylamine salt was obtained.

In a mixture of 30 ml. of hexametapol and 30 ml. of dichloromethane was dissolved 2.15 g. of 2-hydroxy-5-phenylnicotinic acid and after adding to the solution 1.45 ml. of triethylamine, the mixture was cooled to −15°C. Then, 0.95 ml. of ethyl chlorocarbonate was added to the solution and the mixture was stirred for 1.5 hours at −10° to −15°C.

To the solution prepared was added slowly the dichloromethane solution of ampicillin triethylamine salt at temperatures lower than −10°C., the mixture was stirred for 1 hour at the same temperature and then allowed to stand overnight at temperatures lower than −10°C.

The reaction mixture was mixed with water and then a 42% phosphoric acid solution was added to adjust pH to 2 and then the dichloromethane phase formed was recovered. By treating the as in Example 49, 3.5 g. of a white powder of α-(2-hydroxy-5-phenylnicotinoylamino)benzylpenicillin sodium was obtained.

Melting point: 234°–237°C. (decomp.)

Infrared absorption spectrum: $\nu_{max}^{KBr}$ cm.$^{-1}$: 3400 broad (NH,OH), 1770 (β-lactam), 1670 amide), 1600 (carboxylate).

Nuclear magnetic resonance spectrum (D$_6$-DMSO+D$_2$O): δ: 1.5 (6H, d,

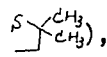

3.96 (1H, s,

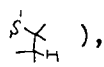

5.40 (2H, d,

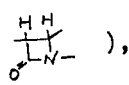

5.95 (1H, s,

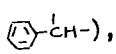

7.45 (5H,

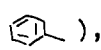

8.15 (1H, d,

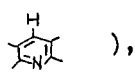

8.65 (1H, d,

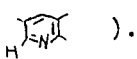

EXAMPLE 57

After stirring a mixture of 4 g. of ampicillin trihydrate, 2 g. of anhydrous magnesium sulfate, 2.4 ml. of triethylamine, and 50 ml. of dichloromethane for 1 hour at room temperature, the magnesium sulfate was filtered off to provide a dichloromethane solution of ampicillin triethylamine salt.

The solution thus prepared was cooled to −20°C. and after adding thereto 2.7 g. of 4-hydroxynicotinoyl chloride and 2.4 ml. If triethylamine, the mixture was stirred for 2 hours at the same temperature and allowed to stand overnight at −20°C.

Dichloromethane was distilled off under a reduced pressure from the reaction mixture and the residue was dissolved in 50 ml. of cold water. Then, 40 ml. of ethyl acetate and 10 ml. of n-butanol was added in layer to the solution and the system was adjusted to pH 3.0 by adding dilute hydrochloric acid, whereby a precipitate was formed. After thoroughly stirring the system, the resulting precipitates were recovered by filtration, dried over phosphorus pentaoxide, and dissolved in 100 ml. of methanol. When an n-butanol solution of 30% potassium 2-ethylhexanoate was added to the solution and then 200 ml. of ether was added thereto crystals were formed. The crystals were recovered by filtration to provide 3.5 g. of white crystals of α-(4-hydroxynicotinoylamino)benzylpenicillin potassium.

Melting point: 243°–247°C. (decomp.).

Infrared absorption spectrum: $\nu_{max}^{KBr}$ Cm.$^{-1}$: 3250 3430 (OH, NH), 1780 (β-lactam), 1660 (amide), 1600 (carboxylate).

Nuclear magnetic resonance spectrum (D$_6$-DMSO + D$_2$O) δ: 1.43, 1.54 (6H,

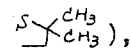

4.00 (1H, s,

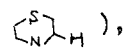

5.43 (2H, q,

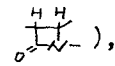

5.98 (1H, s,

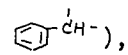

6.57 (1H, d,

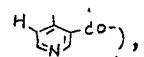

7.48 (5H,

7.92 (1H, d,

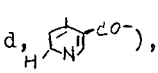

8.57 (1H, s,

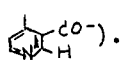

EXAMPLE 58

After stirring a mixture of 8.0 g. of ampicillin trihydrate, 6 g. of anhydrous magnesium sulfate, 4.2 ml. of triethylamine, and 120 ml. of dichloromethane for 1 hour at room temperature, the magnesium sulfate was filtered off to provide a dichloromethane solution of ampicillin triethylamine salt.

In a mixture of 150 ml. hexametapol and 50 ml. of dichloromethane was suspended 3.1 of 2,6-dihydroxyisonicotinic acid and then 2.85 ml. of triethylamine was dissolved in the suspension by heating. Then, 1.9 ml. of ethyl chlorocarbonate was added dropwise to the solution at −20°C. and the mixture was stirred for 1 hour.

To the solution thus prepared was added dropwise the dichloromethane solution of ampicillin triethylamaine salt prepared in the aforesaid step at −20° to −10°C. and after stirring the mixture for 30 minutes, the mixture was allowed to stand overnight at 5°C.

The reaction mixture was adjusted to pH 2.0 with the addition of dilute phosphoric acid and then the dichloromethane phase formed was recovered. The dichloromethane phase was washed with water, dried over anhydrous magnesium sulfate, and dichloromethane was distilled off under a reduced pressure. The residue was dissolved in ethyl acetate and an n-butanol solution containing 30% sodium 2-ethylhexanoate was added to the solution, whereby precipitates were formed. The precipitates were recovered by filtration to provide 4.2 g. of α-(2,6-dihydroxyisonicotinoylamino)benzylpenicillin disodium.

Melting point: above 300°C.

Infrared absorption spectrum: $\nu_{max}^{KBr}$ cm.$^{-1}$: 3430 (OH, NH), 1765 (β-lactam), 1660 (amide), 1610 (carboxylate).

Nuclear magnetic resonance spectrum (D$_2$O): δ: 1.43 (6H,

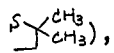

), 4.16 (1H,

), 5.47 (2H,

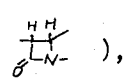

), 5.75 (1H, s,

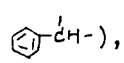

), 7.40 (7H,

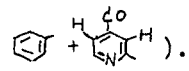

EXAMPLE 59

After stirring a mixture of 4 g. of ampicillin trihydrate, 2 g. of anhydrous magnesium sulfate, 2.4 ml. of triethylamine, and 50 ml. of dicloromethane for 1 hour at room temperature, the magnesium sulfate was filtered off to provide a dichloromethane solution of ampicillin triethylamine salt.

In 10 ml. of dichloromethane was suspended 2.4 g. of 4-hydroxy-5-methoxypicolinic acid and then 2 ml. of triethylamine was dissolved in the suspension. Then, 5 ml. of a dichloromethane solution containing 1.4 ml. of thionyl chloride was added dropwise to the suspension and the mixture was stirred for 1 hour at room temperature.

The suspension thus prepared was added dropwise together with 2.4 ml. of triethylamine to the dichloromethane solution of ampicillin triethylamine salt prepared in the above step at −25°C. with stirring and after stirring for 2 hours at the same temperature, the mixture was allowed to stand overnight at −20°C. Dichloromethane was distilled away from the reaction mixture under a reduced pressure. The residue formed was dissolved in 70 ml. of ice water, 40 ml. of ethyl acetate and 20 ml. of n-butanol were added to the solution in layer, and hydrochloric acid was added to acidify followed by stirring.

The organic solvent phase formed was recovered, washed with water, dried over anhydrous magnesium sulfate, and then n-butanol solution of 30% sodium 2-ethylhexanoate was added, whereby precipitates were formed. The precipitates were recovered by filtration to provide 2.3 g. of α-(4-hydroxy-5-methoxypicolinoylamino)benzylpenicillin sodium.

Melting point: 237°–240°C. (decomp.).

Infrared absorption spectrum: $\nu_{max}^{KBr}$ cm.$^{-1}$: 3380 (OH, NH), 1765 (β-lactam), 1650 (amide), 1610 (carboxylate).

Nuclear magnetic resonance spectrum (D$_6$-DMSO + D$_2$O): δ: 1.43, 1.54 (6H,

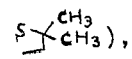

), 3.98 (1H, s

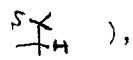

), 5.41 (2H, q,

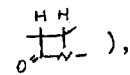

), 5.86 (1H,

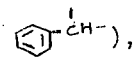

), 7.09 (1H, s, 7.40 (5H, 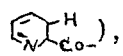, 7.79 (1H, s ), 3.80 (3H, ,

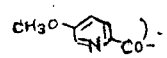

EXAMPLE 60

After stirring a mixture of 12 g. of ampicillin trihydrate, 9 g. of anhydrous magnesium sulfate, 8.4 ml. of triethylamine, and 190 ml. of dichloromethane for 1 hour at room temperature, the magnesium sulfate was filtered away to provide dichloromethane solution of ampicillin triethylamine salt.

In 100 ml. of dichloromethane was suspended 4.23 g. of 4,6-dihydroxynicotinic acid and then 4.2 ml. of triethylamine was dissolved in the suspension. Then, 2.19 ml. of thionyl chloride was added dropwise to the suspension at 0° to −5°C. and the mixture was stirred for 30 minutes at room temperature.

The suspension thus prepared was added dropwise together with 6.3 ml. of triethylamine to the dichloromethane solution of ampicillin triethylamine prepared in the above step with stirring at −20° to −30°C. and thereafter the mixture was stirred for 2 hours at −20°C. ± 5°C. Then, the mixture was allowed to stand overnight at −20°C. The reaction mixture was adjusted to room temperature and dichloromethane was distilled away under reduced pressure. The residue formed was dissolved in 200 ml. of ice water, 100 ml. of ethyl acetate and 70 ml. of n-butanol were placed in the solution in layer, hydrochloric acid was added to acidify, and the orgaic phase formed was recovered. The organic phase was washed with water, dried over anhydrous magnesium sulfate, and then n-butanol solution of 30% sodium 2-ethylhexanoate was added to the solution, whereby precipitates were formed.

*[1] The precipitates were recovered by filtration and dissolved in 150 ml. of ice water and 150 ml. of ethyl acetate and 30 ml. of n-butanol were added to the solution and hydrochloric acid was added to acidify the solution. The organic phase formed was recovered, washed with water, dried over anhydrous magnesium sulfate.
*[2] An then n-butanol solution of 30% sodium, 2-ethylhexanoate was added to the solution, whereby precipitates were formed.

The precipitates were recovered by filtration to provide 4.8 g. of the light-yellow powder of α-(4,6-dihydroxynicotinoylamino)benzylpenicillin disodium.

Melting point: above 300°C.

Infrared absorption spectrum: $\nu_{max}^{KBr}$ cm.$^{-1}$: 3440 (NH, OH), 1765 (β-lactam), 1655 (amide), 1620 (carboxylate).

Nuclear magnetic resonance spectrum ($D_6$DMSO + $D_2$O): δ: 1.43, 1.54 (6H, 5.41 (2H, q, 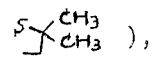),

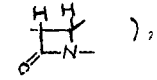, 5.87 (1H, s 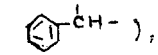, 7.42 (6H, 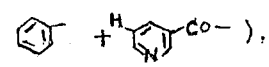, 7.84 (1H, 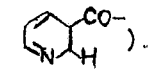.

EXAMPLE 61

After stirring a mixture of 8.0 g. of ampicillin trihydrate, 6 g. of anhydrous magnesium sulfate, 150 ml. of dichloromethane, and 4.2 ml. of triethylamine for 1 hour at room temperature, the magnesium sulfate was filtered away to provide dichloromethane solution of ampicillin triethylamine salt.

In a mixture of 50 ml. of hexametapol and 20 ml. of dichloromethane was suspended 3.15 g. of 5,6-dimethyl-2-hydroxynicotinic acid and dissolved by the addition of 2.8 ml. of triethylamine. Then, 50 ml. of dichloromethane solution of 1.8 ml. of ethyl chlorocarbonate was added dropwise to the suspension at −10°C. and the mixture was stirred for 1 hour.

To the solution thus obtained was added the dichloromethane solution of ampicillin triethylamine salt prepared in the above step at −10°C. and the mixture was stirred for 2 hours at the same temperature.

The reaction mixture was mixed with 200 ml. of cold water and after adjusting the mixture to pH 2 with the addition of hydrochloric acid, the dichloromethane phase formed was recovered. The dichloromethane phase was washed with water, dried over anhydrous magnesium sulfate, and the solvent was distilled away. The residue was dissolved in 200 ml. of ethyl acetate and then butanol solution of 30% sodium 2-ethylhexanoate was added to the solution, whereby a precipitates were formed. The precipitates were recovered by filtration, washed with ether, dried, and then reprecipitated from methanolether to provide 4.5 g of α-(5,6-dimethyl-2-hydroxynicotinoylamino)benzylpenicillin sodium.

Melting point: 231°–233°C. (decomp.).

Infrared absorption spectrum: $\nu_{max}^{KBr}$ Cm$^{-1}$: 3430, 3250 (OH, NH), 1770 (β-lactam), 1660 (amide), 1600 (carboxylate)

Nuclear magnetic resonance spectrum ($D_6$-DMSO + $D_2$O): δ: 1.47, 1.58 (6H, 4.08 (1H, s, 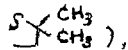

2.10 (3H, s, 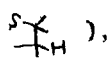

2.33 (3H, s, 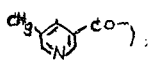

5.50 (2H, q, 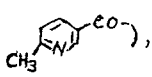

5.95 (1H, s, 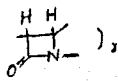

7.50 (5H, 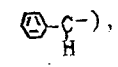

8.24 (1H, s, 

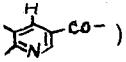

EXAMPLE 62

In a mixture of 450 ml. of ice water and 50 ml. of sodium hydroxide was dissolved 20 g. of ampicillin trihydrate (pH 9.0–9.5). Then, 9 g. of 4,6-dihydroxynicotinic acid azide was added to the solution at 0°–3°C. and the mixture was stirred at the same temperature while adding 1 N sodium hydroxide so that the pH of the reaction product was maintained at 7.5–8.0. After the acid azide was dissolved in the system, the system was further stirred for 1.5 hours at the same temperature. When the reaction mixture having the final pH of 7.0–7.5 was adjusted to pH 3.0 by adding dilute hydrochloric acid, precipitates were formed. The precipitates were recovered by filtration, dissolved in a mixture of n-butanol and ethyl acetate (1 : 2), and after washing the solution with water and drying, n-butanol an solution containing 30% sodium 2-ethylhexanoate was added to the solution, whereby precipitates were formed. The precipitate were recovered by filtration to provide 21 g. of α-(4,6-dihydroxynicotinoylamino)-benzylpenicillin disodium. The product was re-precipitated from methanol-ether. The amount of the final product was 16 g.

Melting point: above 300°C.

Infrared absorption spectrum: $\nu_{max}^{KBr}$ cm.$^{-1}$: 3430 (NH, OH), 1765 (β-lactam), 1655(amide), 1610 (carboxylate).

Nuclear magnetic resonance spectrum (D$_2$O): δ: 1.29, 1.33 (6H, 4.09 (1H, 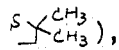

5.35 (2H, 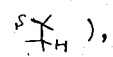

5.51 (1H, 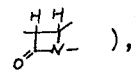

7.28 (5H, 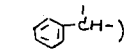

7.93 (1H, 

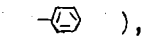

EXAMPLE 63

After stirring a mixture of 4.0 g. of ampicillin trihydrate, 3.0 g. of magnesium sulfate, 2.1 ml. of triethylamine, and 60 ml. of dichloroethane for 1 hour at room temperature, the magnesium sulfate was filtered off to provide a dichloromethane solution of ampicillin triethylamine salt.

To a mixture of 40 ml. of dioxane and 10 ml. of hexametapol was added 1.8 g. of 1,3-dimethyl-2,4-dioxo-1,2,3,4-tetrahydropyrimidine-5-carboxylic acid and then 1.4 ml. of triethylamine was added to the mixture, whereby a transparent solution was formed. Then, 10 ml. of a dioxane solution of 0.9 ml. containing ethyl chlorocarbonate was added dropwise to the solution while cooling the solution to 0°–5°C., the mixture was stirred for 1 hour at 0°–5°C.

To the solution was added dropwise the dichloromethane solution of ampicillin triethylamine salt prepared in the above step at 0°–5°C. and after stirring the mixture for 3 hours at room temperature, the mixture was allowed to stand overnight. After adding to the reaction product dichloromethane and ice water and adjusting to pH 1.5 by adding dilute hydrochloric acid, the dichloromethane phase formed was recovered. The dichloromethane phase was washed three times with water, dried over anhydrous magnesium sulfate, and the solvent was distilled off under a reduced pressure. The residue formed was dissolved in ethyl acetate and an n-butanol solution containing 30% sodium 2-ethylhexanoate was added dropwise to the solution, whereby a precipitate was formed. The precipitate was recovered by filtration (the amount was 4.5 g.) and recrystallized from methanolether to provide a white powder of α-(1,3-dimethyl-2,4-dioxo-1,2,3,4-tetrahydropyrimidine-5-carbonylamino)benzylpenicillin sodium.

Melting point: 223°–228°C. (decomp.).

Infrared absorption spectrum: $\nu_{max}^{KBr}$cm.$^{-1}$: 3430 (NH), 1765 (β-lactam), 1670 (amide, ketone), 1610 (carboxylate).

Nuclear magnetic resonance spectrum (D$_6$ DMSO + D$_2$O): δ: 1.41, 1.53 (6H,

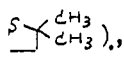

3.26, 3.42 (6H,

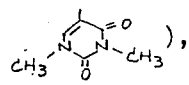

5.41 (2H, q,

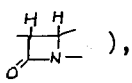

5.85 (1H, d,

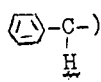

7.38 (5H,

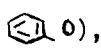

8.43 (1H, s,

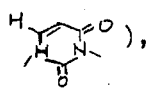

3.98 (1H, s,

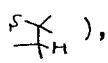

9.92 (1H, d,

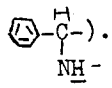

EXAMPLE 64

By treating a mixture of 806 mg. of ampicillin trihydrate, 600 mg. of magnesium sulfate, 0.42 ml. of triethylamine, and 15 ml. of dichloromethane as in Example 63, a dichloromethane solution of ampicillin triethylamine salt was obtained.

To a solution of 312 mg. of 2,4-dioxo-1,2,3,4-tetrahydropyrimidine-5-carboxylic acid in 10 ml. of hexametapol was added 0.28 ml. of triethylamine and after cooling the solution to 0°–5°C., 5 ml. of a dichloromethane solution containing 0.18 ml. of ethyl chlorocarbonate was added dropwise to the solution. Then, the mixture was stirred for one hour at the same temperature.

To the solution thus obtained was added dropwise the dichloromethane solution of ampicillin triethylamine salt for 3 hours at room temperature.

After adding to the reaction product dichloromethane and ice water and acidifying it by adding dilute hydrochloric acid, the dichloromethane phase formed was recovered. The dichloromethane phase was washed three times with water, dried over anhydrous magnesium sulfate, and the solvent was distilled off under a reduced pressure. The residue was dissolved in ethyl acetate and an n-butanol solution containing 30% sodium 2-ethylhexanoate was added dropwise to the solution, whereby a precipitate was formed. The precipitate was recovered by filtration and re-precipitated from methanol-ether to provide 310 mg. of the a white powder of α-(2,4-dioxo-1,2,3,4-tetrahydropyrimidine-5-carbonylamino)benzylpenicillin sodium.

Melting point: 273°C. (decomp.).

Infrared absorption spectrum: $\nu_{max}^{KBr}$cm.$^{-1}$: 3430 (NH,), 1765 (β-lactam), 1650 (amide, ketone), 1600 (carboxylate).

Nuclear magnetic resonance spectrum (D$_6$DMSO + D$_2$O): δ: 1.44, 1.55 (6H,

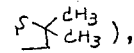

4.02 (1H, s,

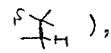

5.41 (2H, q,

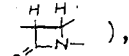

5.80 (1H, s,

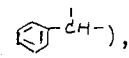

7.41 (5H,

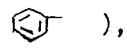

8.44 (1H,

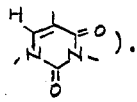).

EXAMPLE 65

By treating a mixture of 8.0 g. of ampicillin trihydrate, 6.0 magnesium sulfate, 4.2 ml. of triethylamine, and 120 ml. of dichloromethane as in Example 63, a dichloromethane solution of ampicillin triethylamine salt was obtained.

In 60 ml. of dichloromethane was dissolved 3.4 g. of 3-methyl-2,4-dioxo-1,2,3,4-tetrahydropyrimidine-5-carboxylic acid and then 2.8 ml. of triethylamine was added to the solution. After cooling the mixture to −20°C., a solution of 1.8 ml. of ethyl chlorocarbonate in 50 ml. of dichloromethane was added dropwise to the mixture and then the resultant mixture was stirred for 1 hour at −20°C.

To the solution prepared was added dropwise the dichloromethane solution of ampicillin triethylamide salt prepared in the above step at −20°C. and then the mixture was stirred for 3 hours at room temperature.

After adding to the reaction product dichloromethane and ice water and adjusting the pH to 1.5 by adding dilute hydrochloric acid, the dichloromethane phase that had formed was recovered, washed three times with water, dried over anhydrous magnesium sulfate, and then the solvent was distilled off under a reduced pressure. The residue formed was dissolved in ethyl acetate and an n-butanol solution containing 30% sodium 2-ethylhexanoate was added to the solution, whereby a precipitate was formed. The precipitate was recovered by filtration and reprecipitated from methanol-ether to provide 4.5 g. of a white powder of α-(3-methyl-2,4-dioxo-1,2,3,4-tetrahydropyrimidine-5-carbonylamino)benzylpenicillin sodium.

Melting point: 252°C. (decomp.).

Infrared absorption spectrum: $\nu_{max}^{KBr}$cm.$^{-1}$: 3430 (NH), 1765 (β-lactam), 1670 (amide, ketone). 1610 (carboxylate).

Nuclear magnetic resonance spectrum (D$_6$DMSO + D$_2$O): δ: 1.45, 1.57 (6H,

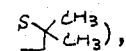, 3.25 (3H, s,

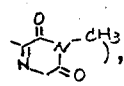, 4.08 (1H, s,

, 5.44 (2H, q,

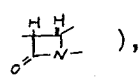, 5.96 (1H, d,

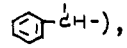, 7.48 (5H,

, 8.42 (1H, s,

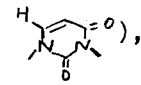, 10.08 (1H, d,

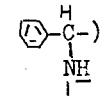

EXAMPLE 66

A mixture of 700 mg. of 4-oxo-2H-pyran-6-carboxylic acid, 0.72 ml. of triethylamine, and 30 ml. of dichloromethane was cooled to −20°C. and after adding dropwise to the solution 0.48 ml. of ethyl chlorocarbonate, the mixture was stirred for 1.5 hours at −20°C.

To the solution thus obtained was added dropwise at −15°C. to −25°C. a dichloromethane solution of ampicillin triethylamine salt prepared by adding 2 g. of ampicillin tri-hydrate, 1.5 g. of magnesium sulfate, and 1.05 ml. of triethylamine to 25 ml. of dichloromethane, stirring the mixture for 1 hour at room temperature, and filtering off the magnesium sulfate. After stirring further the resultant mixture for 1 hour at −10°C., the mixture was allowed to stand overnight at 2°C. After adding to the reaction product a saturated aqueous sodium chloride solution and acidifying it by adding hydrochloric acid, the dichloromethane phase that had formed was recovered. The dichloromethane phase was washed with water, dried over anhydrous magnesium sulfate, and the solvent was distilled away under a reduced pressure. The residue formed was dissolved in ethyl acetate and an n-butanol solution of 30% sodium 2-ethylhexanoate was added to the solution, whereby a precipitate was formed. The precipitate was recovered by filtration to provide 1.0 g. of a white powder of α-(2-oxo-2H-pyran-6-carbonylamino)benzylpenicillin sodium.

Melting point: 214°–220°C. (decomp.)

Infrared abosorption spectrum: $\nu_{max}^{KBr}$ cm.$^{-1}$: 3400 (NH), 1750 (β-lactam), 1665 (lactone, amide), 1600 (carboxylate).

Nuclear magnetic resonance spectrum (D$_6$-DMSO + D$_2$O): : 1.42, 1.50 (6H,

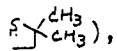, 3.94 (1H, s

, 5.38 (2H, q 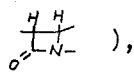), 5.82 (1H, s 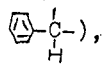), 6.60 (1H, q,
7.09 (1H, q ), 7.40 (6H, 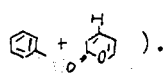).

To a solution of 700 mg. of 4-oxo-4H-pyran-2-carboxylic acid in 30 ml. of dichloromethane was added 0.72 ml. of triethylamine and after cooling the mixture to −10°C. and adding dropwise thereto 0.48 ml. of ethyl chlorocarbonate, the resultant mixture was stirred for 1.5 hours at −20°C. To the solution thus prepared was added dropwise at −10° to −15°C. the dichloromethane solution of ampicillin triethylamine salt prepared by using 2 g. of ampicillin tri-hydrate as in Example 66, then the mixture was stirred for 1 hour at −10°C. and allowed to stand overnight at 2°C.

After adding to the reaction product saturated aqueous sodium chloride solution and acidifying it by adding hydrochloric acid, 30 ml. of butanol was added to the reaction product, and the organic phase formed was recovered. The organic phase was washed three times with saturated aqueous sodium chloride solution, dried over anhydrous magnesium sulfate, and the solvent was distilled off under a reduced pressure. When an n-butanol solution of 30% sodium 2-ethylhexanoate was added dropwise to the residue formed and ether was added thereto, a precipitate was formed. The precipitate was recovered by filtration to provide 0.7 g. of a white powder of α-(4-oxo-4H-pyran-2-carbonylamino)benzylpenicillin sodium.

Melting point: 229°–234°C,. (decomp.).

Infrared absorption spectrum: $\nu_{max}^{KBr}$ cm.$^{-1}$: 3400 (NH), 1760 (β-lactam), 1645 (amide, ketone), 1595 (carboxylate).

Nuclear magnetic resonance spectrum (D$_6$-DMSO + D$_2$O) δ: 1.40, 1.48 (6H, 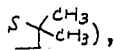), 3.99 (1H, s, ), 5.42(2H, q, 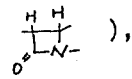), 5.80 (1H, s, 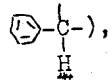), 6.42 (1H, q, 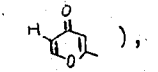), 6.82 (1H, d, 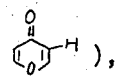), 7.36 (5H, 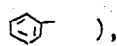), 8.22 (1H, d, 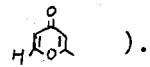).

EXAMPLE 68

A mixture of 1.56 g. of 5-hydroxy-4-oxo-4H-pyran-2-carboxylic acid, 1.45 ml. of triethylamine, 25 ml. of hexametapol and 10 ml. of dichloromethane was cooled to −10°C. and after adding dropwise to the solution 0.95 ml. of ethyl chlorocarbonate, the mixture was stirred for 1 hour at the same temperature as above.

To the solution thus obtained was added dropwise at a temperature lower than 0°C. A dichloromethane solution of ampicillin triethylamine salt prepared by using 4 g. of ampicillin trihydrate as in Example 66. Then the mixture was stirred for two hours at room temperature.

After adding to the reaction product ice water and acidifying the solution to pH 2 by adding hydrochloric acid, the organic phase formed was recovered. The organic phase was washed twice with ice water, dried over anhydrous magnesium sulfate, and the solvent was distilled off under a reduced pressure and was dissolved in ethyl acetate. When a butanol solution containing 30 % sodium 2-ethylhexanoate was added to the solution, a precipitate was formed. The precipitate was recovered by filtration to provide 3.0 g. of a white powder of α-(5-hydroxy-4-oxo-4H-pyran-2-carbonylamino)benzylpenicillin sodium.

Melting point: 225°–231°C (decomp.)

Infrared absorption spectrum: $\nu_{max}^{KBr}$ cm$^{-1}$: 3430 broad (NH, OH), 1765 (lactam), 1660 (amide, ketone), 1610 (carboxylate)

Nuclear magnetic resonance spectrum (CD₃OD) δ: 1.52 (6H, d,

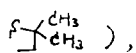), 4.16 (1H, s,

)

5.50 (2H, q,

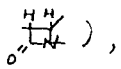), 5.80 (1H, s,

)

7.04 (1H, s,

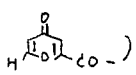)

7.40 (5H, s,

)

7.80 (1H, s,

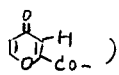)

EXAMPLE 69

To 50 ml. of dichloromethane were added 4.0 g. of ampicillin tri-hydrate, 2 g. of anhydrous magnesium sulfate, and 4.8 ml. of triethyllamine, and after stirring the mixture for about 20 minutes at room temperature, the magnesium sulfate was filtered off to provide a dichloromethane solution of ampicillin triethylamine salt. After cooling the solution to −20°C., 2.2 g. of 4-chloropyridine-3-carobnylchloride hydrochloride was added little by little to the solution at −15° to −20°C. with stirring. After further stirring the mixture at the same temperature for 1 hour, the mixture was concentrated at a low temperature under a reduced pressure. The residue was dissolved in 100 ml. of cold water and the solution was adjusted to pH 2 with hydrochloric acid. The crystals thus precipitated were recovered by filtration, washed with water, dissolved in a mixture of 30 ml. of n-butanol and 60 ml. of ethyl acetate, and then the solution was washed four times each time with 30 ml. of a 5% aqueous sodium chloride solution. After drying the organic phase thus formed over anhydrous magnesium sulfate, an n-butanol solution containing 30% potassium 2-ethylhexanoate was added to the solution until no further precipitation formed. The precipitate was recovered by filtration, washed wit ethyl acetate and then ether, and reprecipitated from methanol-ether to provide 3.5 g. of a light-yellow powdery crystal of α-(4-chloropyridine-3-carbonylamino)benzylpenicillin potassium.

Melting point: 220°–225°C. (decomp.)

Infrared absorption spectrum: $\nu_{max}^{KBr}$cm.$^{-1}$: 3400, 3300 (NH), 1770 (β-lactam), 1650 (amide), 1605 (carboxylate).

Nuclear magnetic resonance spectrum (D₆-DMSO + D₂O) δ: 1.42, 1.54 (6H,

), 3.99 (1H, s,

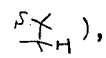), 5.42 (2H,q,

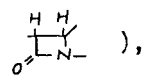), 5.86 (1H, s,

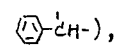), 7.40 (5H,

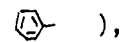), 7.61 (1H, d,

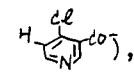), 8.59 (1H, q,

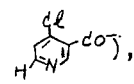), 8.61 (1H, d,

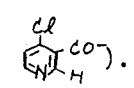).

EXAMPLE 70

By reacting 4.0 g. of ampicillin tri-hydrate and 2.2 g. of 4-chloropyridine-2-carbonylchloride hydrochloride according to the method shown in Example 69, 3.0 g. of a light-yellow powdery crystal of α-(4-chloropyridine-2-carbonylamino)benzylpenicillin sodium was obtained.

Melting point: 222°–228°C. (decomp.).

Infrared absorption spectrum: $\nu_{max}^{KBr}$ cm.$^{-1}$: 3400 (NH), 1770 (β-lactam), 1660 (amide), 1602 (carboxylate).

Nuclear magnetic resonance spectrum (D$_6$-DMSO + D$_2$O): δ: 1.46, 1.56 (6H,

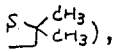), 4.02 (1H,

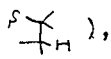), 5.44 (2h, q,

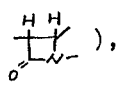), 5.90 (1H, s,

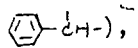), 7.42–7.60 (5H, m,

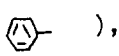), 7.90 (1H, q,

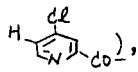), 8.18 (1H, d,

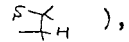)

8.83 (1H, d,

).

EXAMPLE 71

By reacting 4.0 g. of ampicillin tri-hydrate and 2.5 g. of 4-chloro-5-methoxypyridine-2-carbonylchloride hydrochloride according to the method as shown in Example 69, 2.1 g. of α-(4-chloro-5-methoxypyridine-2-carbonylamino)benzylpenicillin sodium was obtained.

Melting point: 250°–270°C. (decomp.).

Infrared absorption spectrum: $\nu_{max}^{KBr}$ cm.$^{-1}$: 3400 (NH), 1765 (β-lactam), 1660 (amide), 1600 (carboxylate).

Nuclear magentic resonance spectrum (D$_6$-DMSO + D$_2$O) δ1.51 (6H,

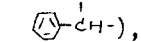, 4.01 (4H, s, CH$_3$O and

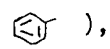), 5,44 (2H, q,

), 5.85 (1H, s,

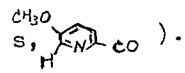), 7.40 (5H, s,

), 8.04 (1H, s,

), 8.50 (1H,

).

EXAMPLE 72

To 60 ml. of dichloromethane were added 4.0 g. of ampicillin tri-hydrate, 3.0 g. of anhydrous magnesium sulfate, and 2.1 ml. of triethylamine and after stirring the mixture for 1 hour at room temperature, the magnesium sulfate was filtered away to provide a dichloromethane solution of ampicillin triethylamine salt.

After cooling the solution prepared thus to −30°C., 1.75 g. of 4-oxo-4H-thiopyran-3-carbonylchloride and 2.1 ml. of triethylamine were added to the solution and the mixture was stirred for 1 hour. Then, after further stirring the mixture at room temperature, dichloromethane was distilled off under a reduced pressure. The residue obtained was mixed with water and after adjusting the pH of it to 2 by adding dropwise 40% phosphoric acid, the reaction product was extracted with 200 ml. of a mixture of butanol and ethyl acetate in a 1:1 by volume ratio. The extract was washed twice with water, washed twice with saturated aqueous sodium chloride solution, dried over anhydrous magnesium sulfate, and then a n-butanol solution containing 30% sodium 2-ethylhaxanoate was added thereto, whereby a precipitate was formed. The precipitate was recovered by filtration, washed with ethyl acetate and then ether, and re-precipitated from methanolether to provide 3.2 g. of α-(4-oxo-4H-thiopyran-3-carbonylamino)benzylpenicillin sodium.

Melting point: 238°–245°C. (decomp.).

adding to the system 50 ml. of isopropanol followed by stirring, the precipitate was recovered by filtration and washed with isopropanol and ether. The precipitate was dissolved in 10 ml. of ice water and adjusted to pH 2 with 10% hydrochloric acid, whereby a precipitate was formed. The precipitate was recovered by filtration, washed with water, dried, and dissolved in 25 ml. of methanol. When 5.7 ml. of an n-butanol solution containing 30% sodium 2-ethylhexanoate was added to the solution and the mixture was diluted with ether, a precipitate was formed. The precipitate was recovered by filtration, washed with ethyl acetate and ether, and dried to provide 1.97 g. of a white powder of D(-)-α-(4,6-dihydroxynicotinoylamino)benzylpenicillin disodium.

Yield: 74.4%
Melting point: above 300°C.

PREPARATION OF THE STARTING MATERIAL

In 60 ml. of 1 N aqueous sodium hydroxide solution were dissolved 6.0 g. of D-α-phenylglycine and 40 g. of ice and then 7.2 g. of 4,6-dihydroxynicotinic acid amide was added to the solution. Then, while stirring the mixture at 0°–5°C., 50 ml. of a 1 N aqueous sodium hydroxide solution was added dropwise to the mixture over a period of about 30 minutes at a pH of 9. After stirring the mixture for 30 minutes at the same temperature, the reaction product was filtered and adjusted to pH 2 with 6 N hydrochloric acid. The crystals that had formed were recovered by filtration, washed with water, and dried to provide 7.7 g. of the white crystals of D-α-(4,6-dihydroxynicotinoylamino)phenylacetic acid.

Yield: 67.3%.

Infrared absorption spectrum: $\nu_{max}^{KBr}$ cm.$^{-1}$ : 3370 broad (OH, NH), 1670, 1630 (carboxylate, amide).

Nuclear magnetic resonance spectrum: δ= 5.52 (1H, d,

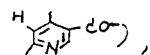

5.66 (1H, s,

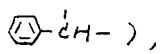

7.22 (5H, m,

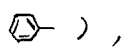

8.14 (1H, s,

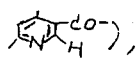

9.31 (1H, d,—NH—)

EXAMPLE 75 a. In 20 ml. of dimethylformamide were dissolved 1.54 g. of 4-oxo-4H-thiopyran-3-carboxylic acid and 5.04 g. of D(-)-α-aminobenzylpenicillin phenacyl ester hydrochloride and then 10 ml. of dimethylformamide solution containing 3.0 g. of diphenylformamide was added to the solution while cooling to 0°C. Then, while stirring the mixture at 0° to −5°C., a solution of 3.1 ml. of triethylamine in 10 ml. of dimethylformamide was added dropwise to the mixture. After stirring the mixture for 1 hour at the same temperature, the resultant mixture was allowed to stand for 24 hours at 0° to 5°C.

The reaction product was dispersed in about 300 ml. of ice water and after adjusting the pH of the dispersion to 2 with 10% hydrochloric acid, the crystals that had formed were recovered by filtration and washed with water. The crystals were dissolved in 100 ml. of ethyl acetate and after washing the solution with water, a 5% aqueous sodium bicarbonate solution, and then water, the solution was dried over anhydrous magnesium sulfate. The ethyl acetate solution thus obtained was concentrated at a low temperature under a reduced pressure and when isopropanol was added to the solid residue followed by stirring, crystals were formed. The crystals were recovered by filtration, washed with a small amount of isopropanol and then ether, and dried to provide 5.5 g. of the yellowish powdery crystals of D(-)-α-(4-oxo-4H-thiopyran-3-carbonylamino)benzylpenicillin phenacyl ester.

Yield: 91.2%.
Melting point: 115°–120°C. (decomp.).

Infrared absorption spectrum: $\nu_{max}^{KBr}$cm.$^{-1}$ : 3300 (NH), 1785 (β-lactam), 1750 (ester), 1700 (ketone), 1660–50 (amide).

Nuclear magnetic resonance spectrum (D$_6$-DMSO) δ= 1.59 (6H, d,

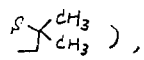

4.44 (1H, s,

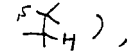

5.56 (2H, q,

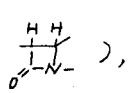

5.93 (1H, d,

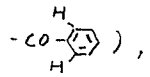

5.64 (2H, s,—O—CH$_2$—CO—)7.4–7.7 (9H,m,

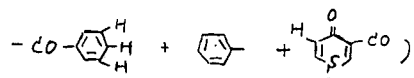

7.98 (2H, d, 8.38 (1H, q,

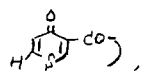

9.33 (1H, d,

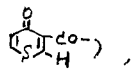

10.79 (1H, d, —NH—)

b. In 10 ml. of dimethylformamide was dissolved 3.02 g. of D(-)-α-(4-oxo-4H-thiopyran-3-carbonylamino)-benzylpenicillin phenacyl ester and while stirring the solution under ice-cooling, 1.3 g. of sodium thiophenolate was added to the solution. After stirring the mixture for 30 minutes at room temperature, the brown reaction product was added to 100 ml. of ice water and adjusted to pH 2 with 10% hydrochloric acid. The precipitate thus formed was collected by filtration, washed with water, and then washed with ether. Then, the viscous reaction product formed was dissolved in 50 ml. of ethyl acetate and after washing the solution with water, the solution was dried and then an n-butanol solution containing 30% sodium 2-ethylhexanoate was added to the solution until no further precipitate formed. The precipitate was collected, washed with ethyl acetate and ether, and re-precipitated from methanol-ether to provide 1.31 g. of a brownish powder of D(-)-α-(4-oxo-4H-thiopyran-3-carbonylamino)-benzylpenicillin sodium.

Yield: 52%.

Melting point 238°–245°C. (decomp.).

Infrared absorption spectrum: $\nu_{max}^{KBr}$cm.$^{-1}$ : 3430 (NH), 1770 (β-lactam), 1660 (amide) 1600 (carboxylate)

Nuclear magnetic resonance spectrum (CD$_3$OD): δ= 1.50 (6H, d,

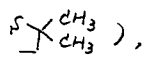

4.15 (1H, s,

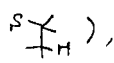

5.45 (2H, q,

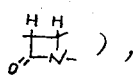

5.76 (1H, s,

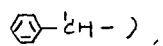

7.40 (6H,

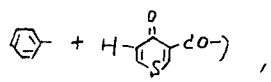

8.27 (1H, q,

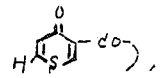

9.32 (1H, d,

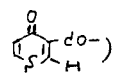

PREPARATION OF THE STARTING MATERIAL

In 200 ml. of dichloromethane was dissolved 18.1 g. of benzylpenicillin phenacyl ester and after adding to the solution 20 ml. of N,N-dimethylaniline, the mixture was cooled to −25°C. Then, 10 g. of phosphorus pentachloride was added to the mixture and the resultant mixture was stirred for 1.5 hours at −25° ± 5°C. Thereafter, 160 ml. of methanol was added dropwise to the mixture at the same temperature and the resultant mixture was further stirred for 3 hours to provide the iminoether solution. To the solution was added 28 ml. of N,N-dimethylaniline and after cooling the mixture to −40° to −45°C., 10 g. of D(-)-α-phenylglycylchloride hydrochloride was added thereto. Then, after stirring the mixture for 3 hours at the same temperature, the mixture was allowed to stand overnight at −20° to −25°C.

After adding to the reaction product 200 ml. of a cold saturated sodium chloride solution and stirring well the mixture at tempertures below 0°C., the aqueous phase formed was separated from the dichloromethane phase. The dichloromethane phase was washed with a cold saturated aqueous sodium chloride solution, dried over anhydrous magnesium sulfate, and concentrated at a low temperature under a reduced pressure. The oily residue formed was washed three times each with 50 ml. of ethyl acetate and then ether was added to the product, whereby crystals were formed. The crystals were collected by filtration and dried to provide 18.1 g. of a yellowish powder of D(-)-α-aminobenzylpenicillin phenacyl ester hydrochloride.

Yield: 89.7%.

Infrared absorption spectrum: $\nu_{max}^{KBr}$cm.$^{-1}$ : 3350 (NH), 3180 (—N$^+$H—), 1785 (β-lactam), 1760 (ester), 1700, 1690 (ketone, amide).

Nuclear magnetic resonance spectrum (CD$_3$OD): δ= 1.59 (1H, s,

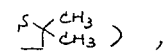

4.53 (H, s,

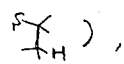

5.18 (1H, s,

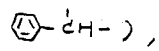, 5.56 (2H, q,

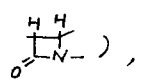, 7.35–7.7 (8H,m,

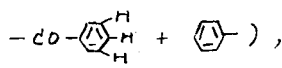, 8.02 (2H,d,

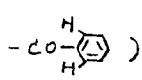 )

By following the same procedure as above, D(-)-α-aminobenzylpenicillin p-bromophenacyl ester hydrochloride and D(-)-α-aminobenzylpenicillinbis-p-methoxyphenyl methyl ester hydrochloride were prepared from the corresponding benzylpenicillin esters.

EXAMPLE 76 a. In a mixture of 60 ml. of dimethylformamide and 20 ml. of water was dissolved 5.83 g. of D(-)-α-aminobenzylpenicillin p-bromophenacyl ester hydrochloride and then 2.8 ml. of triethylamine was added to the solution under ice-cooling. To the solution was added 1.8 g. of 4,6-dihydroxynicotinic acid azide and while stirring at 0°–5°C. 1.4 ml. of triethylamine was added little by little to the mixture to maintain the pH to 8–8.5. After further stirring the mixture for 2 hours at the same temperature, the reaction product was dispersed in 300 ml. of ice water and the dispersion was adjusted to pH 2 with 10% hydrochloric acid. The precipitated crystals were collected and dissolved in 100 ml. of ethyl acetate. Then, the insoluble materials were filtered off. The filtrate was washed with water, dried over anhydrous magnesium sulfate, and then the solvent was distilled off at a low temperature and under a reduced pressure. The solid residue obtained was dissolved in a small amount of dichloromethane and ether was added to the solution, whereby crystals were formed. The crystals were recovered by filtration, washed with ether, and dried to provide 5.5 g. of white crystals of D(-)-α-(4.6-dihydroxynicotinoylamino)benzylpenicillin p-bromophenacyl ester.

Yield: 80.4%.

Melting point: 163°–165°(decomposed).

Infrared absorption spectrum: $\nu_{max}^{KBr}$ cm$^{-1}$ = 3300 broad (OH,NH), 1780 (β-lactam), 1760 (ester), 1700 (ketone), 1660–1630 (ketone, amide)

Nuclear magnetic resonance spectrum (D$_6$DMSO + D$_2$O): δ= 1.53, 1.60 (6H,

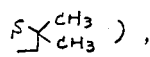 ), 4.59 (1H, s

 )

5.54 (2H, q,

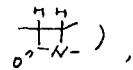), 5.60 (2H, s, —O—CH$_2$—CO—)5.88 (1H, s

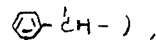, 7.47 (7H, m,

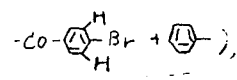, 7.86 (2H, q,

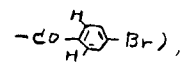, 8.21 (1H, s,

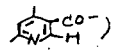)

b. In 20 ml. of dimethylformamide was dissolved 3.42 g. of D(-)-α-(4,6-dihydroxynicotinoyl)benzylpenicillin p-bromophenacyl ester and then 2.0 g. of sodium thiophenolate was added to the solution with stirring under ice-cooling. When the mixture was stirred for 15 minutes at room temperature, a precipitate was formed. After adding to the mixture 50 ml. of isopropanol followed by stirring, the precipitate was collected by filtration and washed with isopropanol and ether. The precipitate was dissolved in 50 ml. of ice water and the solution was saturated with sodium chloride. The solution was adjusted to pH 2 with 10% hydrochloric acid and the precipitate that had formed was extracted with 60 ml. of a mixture of n-butanol and ethyl acetate in a 2:1 by volume ratio. The extract was washed with a 20% aqueous sodium chloride solution, dried over anhydrous sodium sulfate, and then a n-butanol solution containing 30% sodium 2-ethylhexanoate was added to it until no further precipitate formed. The precipitate was collected by filtration, washed with ethyl acetate and ether, and dried to provide 1.95 g. of the white powder of D(—)-α-(4,6-dihydroxynicotinoylamide)-benzylpenicillin disodium.

Yield: 73.5%

Melting point: above 300°C.

Infrared absorption spectrum: $\nu_{max}^{KBr}$ cm$^{-1}$ : 3430 (NH,OH), 1765 (β-lactam), 1655 (amide), 1610 (carboxylate)

Nuclear magnetic resonance spectrum (D$_2$O) δ: 1.29, 1.33 (6H,

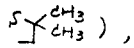, 4.09 (1H, S, 5.35 (2H, q, ), 5.51 (1H, S, 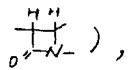), 7.28 (5H, 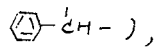), 7.93 (1H, S, 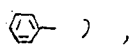)

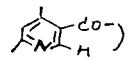

EXAMPLE 77 a. To a solution of 1.56 g. of 2,4-dioxo-1,2,3,4-tetrahydropyrimidine-5-carboxylic acid in 40 ml. of hexamethyl phosphoramide was added 1.4 ml. of triethylamine and after cooling the mixture to 0°–5°C., 10 ml. of a dichloromethane solution containing 1.0 ml. of ethyl chlorocarbonate was added dropwise to the mixture with stirring and the resultant mixture was stirred for 1 hour at the same temperature.

To the mixture was added 40 ml. of dichloromethane solution containing 5.04 g. of D(-)-α-aminobenzylpenicillin phenacyl ester hydrochloride and 1.55 ml. of triethylamine at 0° to −5°C. and then the mixture was stirred for 3 hours at room temperature. The reaction product was concentrated at a low temperature and under a reduced pressure and then concentrate was poured into about 100 ml. of ice water, whereby a yellow viscous material was formed. The material was separated by decantation and dissolved in 100 ml. of ethyl acetate. The solution was washed with 1% hydrochloric acid, 5% aqueous sodium bicarbonate solution, and then water and then dried over anhydrous sodium sulfate. The ethyl acetate solution was concentrated at a low temperature under a reduced pressure and then isopropanol was added to the concentrate, whereby crystals were formed. The crystals were recovered by filtration, washed with isopropanol and ether, and dried to provide 2.4 g. of light-yellow crystals of D(-)-α-(2,4-dioxo-1,2,3,4-tetrahydropyrimidine-5-carbonylamino)benzylpenicillin phenacyl ester.

Yield: 39.7%

Melting point: 146°–148°C. (decomposed).

Infrared absorption spectrum: $\nu_{max}^{KBr}$ cm$^{-1}$: 3300 (NH), 1780 (β-lactam), 1760 (ester), 1705, 1690, 1650 (ketone, amide)

Nuclear magnetic resonance spectrum (D$_6$-DMSO): δ: 1.52, 1.60 (6H, 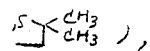), 4.43 (1H, S, 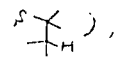), 5.51 (2H, q, 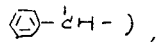), 5.87 (1H, d, ), 7.20–7.70 (8H, m, 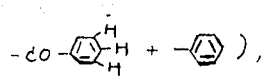), 7.95 (2H, d, 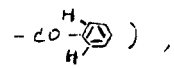), 8.11 (1H, S, 9.34, 9.73 (1H, d, NH)

b. In 5 ml. of dimethylformamide was dissolved 1.52 g. of D(-)-α-(2,4-dioxo-1,2,3,4-tetrahydropyrimidine-5-carbonylamino)benzylpenicillin phenacyl ester and after adding to the solution 0.66 g. of sodium thiophenolate under ice-cooling, the mixture was stirred for 20 minutes at room temperature. The solidified reaction product was dissolved in 50 ml. of ice water and the aqueous solution was washed with ether and adjusted to pH 2 with 10% hydrochloric acid. The precipitate thus formed was collected by filtration, washed with water and then ether, and the viscous reaction product thus obtained was dissolved in 20 ml. of ethyl acetate. The solution was washed with water, dried over anhydrous sodium sulfate and then an n-butanol solution containing 30% sodium 2-hexanoate was added to the solution until no further precipitate formed.

The precipitate thus formed was collected by filtration, washed with ethyl acetate and ether, and dried to provide 0.85 g. of white powder of D(-)-α-(2,4-dioxo-1,2,3,4-tetrahydropyrimidine-5-carbonylamino)benzylpenicillin sodium.

Yield: 66.5%.

Melting point: 273°C. (decomp.).

Infrared absorption spectrum: $\nu_{max}^{KBr}$ cm$^{-1}$: 3430 (NH), 1765 (β-lactam) 1650 (amide, ketone), 1600 (carboxylate)

Nuclear magentic resonance spectrum (D$_6$-DMSO + D$_2$O) δ: 1.44, 1.55 (6H,

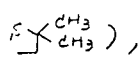

), 4.02 (1H, S,

)

5.41 (2H, q,

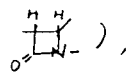

), 5.80 (1H, S,

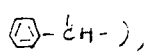

, 7.41 (5H, m,

), 8.44 (1H, S,

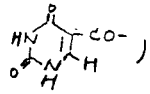

)

EXAMPLE 78 a. In 40 ml. of hexamethyl phosphoramide was suspended 1.89 g. of 4-quinolone-3-carboxylic acid and then 1.4 ml. of triethylamine was dissolved in the suspension. After cooling the suspension to 0°–5°C., 10 ml of a dichloromethane solution containing 1.0 ml. of ethyl chlorocarbonate was added dropwise to the suspension with stirring and the mixture was stirred for 1 hour at the same temperature.

After adding dropwise to the reaction product 40 ml. of a dichloromethane solution containing 5.04 g. of D(-)-α-aminobenzylpenicillin phenacyl ester hydrochloride and 1.55 ml. of triethylamine at 0° to −5°C., the mixture was stirred for 3 hours at room temperature.

The reaction product was concentrated at a low temperaure under a reduced pressure, the concentrate was dispersed in about 100 ml. of ice water, the viscous material that had formed was separated by decantation, and then dissolved in 100 ml. of ethyl acetate. The ethyl acetate solution was washed with 1% hydrochloric acid, 5% aqueous sodium bicarbonate solution, and then water and then dried over anhydrous magnesium sulfate. The solution was concentrated at a low temperature under a reduced pressure and then ether was added to the concentrate, whereby crystals were formed. The crystal was recovered by filtration, washed with ether, and dried to provide 2.8 g. of a light-yellow crystal of D(-)-α-(4-quinolone-3-carbonylamino)benzylpenicillin phenacyl ester.

Yield: 44%.
Melting point: 126°–129°C. (decomposed)
Infrared absorption spectrum: $\nu_{max}^{KBr}$ cm$^{-1}$ : 3250 broad (NH), 1780 (β-lactam), 1760 (ester), 1700, 1660–1640 (ketone, amide)
Nuclear magnetic resonance spectrum (D$_6$-DMSO); δ: 1.58, 1.68 (6H,

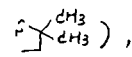

), 4.52 (1H, S,

)

5.60 (2H, q,

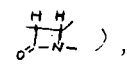

), 5.67 (2H, S, —O—CH$_2$—CO—), 6.06 (1H, d,

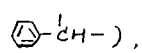

, 7.3–7.7 (12H, m, aromatic ring) 8.02 (2H, d,

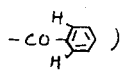

, 8.36, 9.40 (1H, d, NH), 8.80 (1H, S,

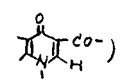

)

b. In 10 ml. of dimethylformamide was dissolved 1.6 g. of D(-)-α-(4-quinolone-3-carbonylamino)benzylpenicillin phenacyl ester and while stirring under ice-cooling, 0.66 g. of sodium thiophenolate was added to the solution. After stirring the mixture for 10 minutes at room temperature, 50 ml. of ethyl acetate was added to the mixture. The precipitate that had formed was collected by filtration, washed with ethyl acetate, and dissolved in 20 ml. of ice water. The aqueous solution was adjusted to pH 2 with 10% hydrochloric acid and the precipitate that had formed was separated by decantation and washed with ether. The viscous product thus obtained was dissolved in 20 ml. of a mixture of n-butanol and ethyl acetate in a 2:1 by volume ratio and the solution was washed with 20% aqueous sodium chloride solution and dried over anhydrous sodium sulfate. Then an n-butanol solution containing 30% sodium 2-ethylhexanoate was added to the solution until no further precipitate formed. The precipitate was collected by filtration, washed with ethyl acetate and ether, and dried to give 0.87 g. of a white powdery crystal of D(-)-α-(4-quinolone-3-carbonylamino)benzylpenicillin sodium.

Yield: 64.2%.
Melting point: 221°–226°C. (decomposed)

Infrared absorption spectrum: $\nu_{max}^{KBr}$ cm$^{-1}$: 3400 broad (NH), 1765 (β-lactam), 1660–1630 (amide, ketone), 1600 (carboxylate)

Nuclear magentic resonance spectrum (CD$_3$OD): δ: 1.54, 1.58 (6H,

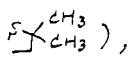

), 4.24 (1H, S,

), 5.57 (2H, q,

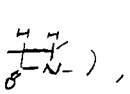

), 5.92 (1H, S,

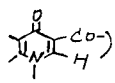

), 7.3–7.7 (9H, m, aromatic ring), 8.82 (1H, S,

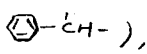

EXAMPLE 79 a. In a mixture of 25 ml. of hexamethyl phosphoramide and 10 ml. of dichloromethane was suspended 1.56 g. of 5-hydroxy-4-oxo-4H-pyran-2-carboxylic acid and then 1.4 ml. of triethylamine was dissolved in the suspension. After cooling the solution to 0°–5°C., 10 ml. of dichloromethane solution containing 1,0 ml. of ethyl chlorocarbonate was added dropwise to the solution and then the mixture was stirred for 1 hour at the same temperature.

After adding dropwise to the reaction product 40 ml. of a dichloromethane solution containing 5.04 g. of D(-)-α-aminobenzylpenicillin phenacyl ester hydrochloride and 1.55 ml. of triethylamine at 0° to −5°C., the resultant mixture was stirred for 3 hours at room temperature. The reaction product was concentrated at a low temperature under a reduced pressure and the concentrate was added to about 100 ml. of ice water, whereby a light-brown viscous material was formed. The product was separated by decantation and dissolved in 100 ml. of ethyl acetate. The ethyl acetate solution was washed with 1% hydrochloric acid, 5% aqueous sodium bicarbonate solution, and then water and then dried over anhydrous magnesium sulfate. The ethyl acetate solution was concentrated at a low temperature under a reduced pressure and the solid residue that had formed was dissolved in a small amount of dichloromethane. After adding to the solution isopropanol to make the solution turbid, the solution was concentrated at a low temperature under a reduced pressure, whereby yellow crystals were formed. The crystal were recovered by filltration, washed with a small amount of isopropanol and then ether, and dried to give 4.17 g. of a light-yellow crystal of D(-)-α-(5-hydroxy-4-oxo-4H-pyran-2-carbonylamino)benzylpenicillin phenacyl ester.

Yield: 69%.

Melting point: 128°–130°C. (decomposed).

Infrared absorption spectrum: $\nu_{max}^{KBr}$ cm$^{-1}$: 3330–3400 (NH, OH), 1780 (β-lactam), 1755 (ester), 1700, 1690, 1670, 1640 (ketone, amide)

Nuclear magnetic resonance spectrum (D$_6$-DMSO): δ: 1.60 (6H, d,

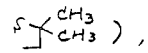

), 4.50 (1H, S,

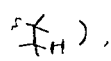

), 5.57 (2H, q,

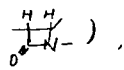

), 5.90 (1H, d,

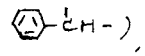

), 5.69 (2H, S, —O—CH$_2$—CO—), 7.00 (1H, S,

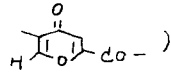

)

7.3–7.7 (8H, m, aromatic ring) 8.04 (2H, d,

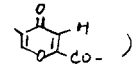

), 8.20 (1H, S,

)

9.07, 9.32 (1H, d, —NH—)

b. In 10 ml. of dimethylformamide was dissolved 3.03 g. of D(-)-α-(5-hydroxy-4-oxo-4H-pyran-2-carbonylamino)benzylpenicillin phenacyl ester and while stirring the solution under ice-cooling, 2,0 g. of sodium thiophenolate was added thereto. When the mixture was stirred for 20 minutes at room temperature, an oily material was formed. To the reaction product was added 50 ml. of acetone followed by stirring and the precipitate that had formed was collected by filtration and washed with a small amount of ether. The precipitate was dissolved in 20 ml. of ice water and the solution was adjusted to pH 2 with 10% hydrochloric acid. Then, the precipitate that had formed was collected by filtration, washed with water and a small amount of ether, and dissolved in ethyl acetate. The ethyl acetate solution was washed with water, dried over anhydrous magnesium sulfate, and an n-butanol solution containing 30% sodium 2-ethylhexanoate was added to the solution until no further precipitate formed. The precipitated formed was collected by filtration, washed with ethyl acetate and ether, and dried to provide 1.3 g. of a yellowish powder of D-(-)-α-(5-hydroxy-4-oxo-4H-pyran-2-carbonylamino)benzylpenicillin disodium.

Yield: 49%,

Melting point: 225°–231°C. (decomposed).

Infrared absorption spectrum: $\nu_{max}^{KBr}$ cm$^{-1}$ : 3430 broad (NH, OH), 1765 (β-lactam), 1660 (amide, ketone), 1610 (carboxylate)

Nuclear magnetic resonance spectrum (CD$_3$OD) δ: 1.52 (6H, d,

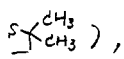

4.16 (1H, S,

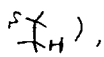

5.50 (2H, q,

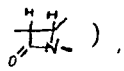

5.80 (1H, S,

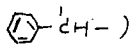

7.04 (1H, S,

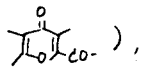

7.40 (5H, S,

7.80 (1H, S,

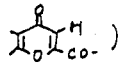

EXAMPLE 80 a. In a mixture of 40 ml. of dimethylformamide and 10 ml. of water was dissolved 3.05 g. of D(-)-α-aminobenzylpenicillin bis(p-methoxyphenyl)methyl ester hydrochloride and then 1.4 ml. of triethylamine was added to the solution under ice-cooling. To the solution was added 0.9 g. of 4,6-dihydroxynicotinic acid amide and while stirring the mixture at 0°–5°C., 0.7 ml. of triethylamine was added thereto little by little to maintain the pH thereof to 8–8.5. After further stirring the mixture for 2 hours at the same temperature, the reaction product was dispersed in about 150 ml. of ice water, the dispersion was adjusted to pH 2 with 10% hydrochloric acid, and the precipitate that had formed was extracted with 50 ml. of ethyl acetate. The insoluble materials were filtered off and the filtrate was washed with water and dried over anhydrous magnesium sulfate. The filtrate was concentrated at a low temperature under a reduced pressure and ether was added to the concentrate, whereby crystals were formed. The crystal were collected by filtration, washed with ether, and dried to give 2.25 g. of a light-yellow crystal of D(-)-α-(4,6-dihydroxynicotinoylamino)benzylpenicillin bis(p-methoxyphenyl)methyl ester.

Yield: 63.2%

Melting point: 156°–159°C. (decomp.).

Infrared absorption spectrum: $\nu_{max}^{KBr}$ cm$^{-1}$ : 3340 (broad, OH, NH), 1785 (β-lactam), 1740 (ester), 1660, 1635 (amide)

Nuclear magnetic resonance spectrum (D$_6$-DMSO) δ: 1.18, 1.52 (6H,

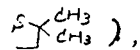

3.73 (3H, S, —O—CH$_3$) 4.48 (1H, S,

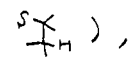

5.57 (2H, q,

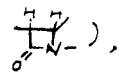

5.86 (1H, d,

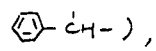

1.88 (1H, S, —CH<), 6.90 (4H, d,

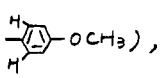

7.28 (5H, S,

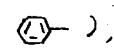

7.32 (4H, d,

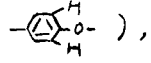

8.10, 9.09 (1H, d, —NH—)

b. In 8 ml. of acetone was dissolved 1.0 g. of D(-)--(4,6-dihydroxynicotinoylamino)benzylpenicillin bis(p-methoxyphenyl)methyl ester and after adding to the solution 2 ml. of 1 N hydrochloric acid, the mixture was stirred for 5 hours under ice-cooling. The reaction product was added to 20 ml. of 2% aqueous sodium bicarbonate solution and washed with 20 ml. of ethyl acetate. The aqueous phase that had formed was separated and after saturating it with sodium chloride, the aqueous solution was adjusted to pH 2 with 10% hydrochloric acid. Then, the product was extracted with 10 ml. of a mixture of ethyl acetate and n-butanol in a 2:1 by volume ratio. The organic phase that had formed was separated, washed with saturated aqueous sodium chloride solution, and dried over anhydrous magnesium sulfate. Thereafter, n-butanol an solution containing 30% sodium 2-ethylhexanoate was added to the solution until no further precipitate formed. The precipitate thus formed was collected by filtration, washed with a small amount of ethyl acetate and ether, and dried to provide 0.16 g. of D(-)-α-(4,6-duhydroxynicotinoylamino)benzylpenicillin disodium.

Yield: 21.4%

EXAMPLE 81 a. In 60 ml. of dichloromethane was dissolved 5.83 g. of D(-)-α-aminobenzylpenicillin p-bromophenacyl ester hydrochloride and after cooling the solution to −20°C., 3.1 ml. of triethylamine was added thereto. To the solution added little by little 2.6 g. of 4-chloro-5-methylpyridine-2-carbonylchloride hydrochloride and then the mixture was stirred for 2 hours at 0° to −5°C. The reaction product was concentrated at a low temperature under a reduced pressure and the residue that had formed was dissolved in 100 ml. of ethyl acetate. The solution was washed with ice water and then 2% cold hydrochloric acid, washed further with water, and dried over anhydrous magnesium sulfate. The solution was concentrated under a reduced pressure and the residue that had formed was crystallized from dichloromethaneether. The crystals were collected by filtration and washed with a small amount of ether to provide 3.8 of a light-yellow fine powder of D(-)-α-(4-chloro-5-methoxypyridine-2-carbonylamino)benzylpenicillin p-bromophenacyl ester.

Yield: 53.2%

Melting point: 115°–118°C. (decomp.).

Infrared absorption spectrum: $\nu_{max}^{KBr}$ cm$^{-1}$ : 3370 (NH), 1785 (β-lactam), 1760 (ester), 1700 (ketone), 1670–1660 (amide)

Nulcear magnetic resonance spectrum (D$_6$-DMSO) δ: 1.59 (6H, d,

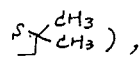

4.10 (3H, S, CH$_3$O—), 4.47 (1H, S,

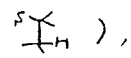

5.57 (2H, q,

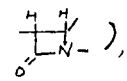

5.64, (2H, S, —O—CH$_2$—CO—), 5.92 (1H, d,

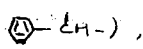

7.30–7.60 (7H, m,

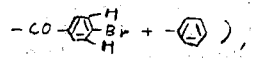

7.87 (2H, q,

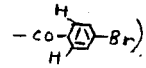

8.04 (1H, S,

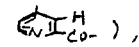

8.60 (1H, S,

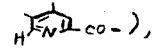

8.92, 9.44 (1H, d, —NH—)

b. In 16 ml. of dimethylformamide was dissolved 3.58 g. of D(-)-α-(4-chloro-5-methoxypyridine-2-carbonylamino)benzylpenicillin p-bromophenacyl ester and after adding to the solution 1.3 g. of thiophenol sodium salt under ice-cooling, the mixture was stirred for 20 minutes at room temperature.

The reaction product was dispersed in 50 ml. of ice water and the dispersion was adjusted to pH 2 with 10% hydrochloric acid. The precipitate that had formed was collected by filtration, washed with water and ether, and dissolved in 50 ml. of a mixture of ethyl acetate and n-butanol in a 2:1 by volume ratio. The solution was washed with aqueous sodium chloride solution, dried over anhydrous magnesium sulfate, an n-butanol solution containing 30% sodium 2-ethylhexanoate was added to the solution until no further precipitate formed. The precipitate was recovered by filtration, washed with ethyl acetate and ether, and dried to give 1.35 g. of a light-yellow powdery crystals of D(-)-α-(4-chloro-5-methoxypyridine-2-carbonylamino)benzylpenicillin sodium.

Yield: 50.0%

Melting point: 250°–270°C. (decomp.).

Infrared absorption spectrum: $\nu_{max}^{KBr}$ cm$^{-1}$ : 3400 (NH), 1765 (β-lactam), 1660 (amide), 1600 (carboxylate).

Nuclear magnetic resonance spectrum (D$_6$-DMSO + D$_2$O): δ: 1.51 (6H,

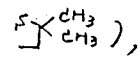

4.01 (4H, S, CH$_3$O- +

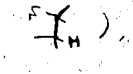

5.44 (2H, q, 5.85 (1H, S, 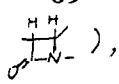

7.40 (5H, S, 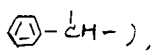

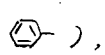

8.04 (1H, S, 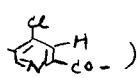

8.50 (1H,  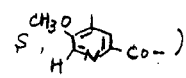

What is claimed is:
1. D-α-(4-quinolone-3-carbonylamino--)-benzylpenicillin sodium.
2. D-α-(7-dimethylamino-4-quinolone-3-carbonylamino--)-benzylpenicillin potassium.
3. D-α-(4-hydroxynicotinoylamino)-benzylpenicillin potassium.
4. D-α-(4-hydroxy-5-methoxypicolinoylamino)-benzylpenicillin sodium.
5. D-α-(4,6dihydroxynicotinoylamino)-benzylpenicillin disodium.
6. D-α-(2,4-dioxo-1,2,3,4-tetrahydropyrimidinecarbonylamino)benzylpenicillin sodium.
7. D-α-(5-hydroxy-4-oxo-4H-pyran-2-carbonylamino)-benzylpenicillin sodium.
8. D-α-(4-oxo-4H-thiopyran-3-carbonylamino)-benzylpenicillin sodium.

* * * * *

UNITED STATES PATENT OFFICE
CERTIFICATE OF CORRECTION

Patent No. 3,953,428          Dated April 27, 1976

Inventor(s)      Masuo Murakami, et al          Page 1 of 6

It is certified that error appears in the above-identified patent and that said Letters Patent are hereby corrected as shown below:

In the Abstract of the Disclosure, 2nd column, line 2: Change "the position" to --the 3-position--;

line 7 after first formula: "a" (1st occurrence) should be --an--.

line 1 after second formula: "thiazole" should be --thiazolo--.

UNITED STATES PATENT OFFICE
CERTIFICATE OF CORRECTION

Patent No. 3,953,428   Dated April 27, 1976

Inventor(s) Masuo Murakami, et al   Page 2 of 6

It is certified that error appears in the above-identified patent and that said Letters Patent are hereby corrected as shown below:

In the Abstract of the Disclosure, 2nd column, line 6 after formula (4): "portion" should be --position--, "(+0)" should be --(-0)--.

Column 1, line 36: "λ" should be deleted.

line 13: Insert --indicated-- after "the".

Column 11, line 1: "phosphor" should be --phosphoramide--.

Column 15, line 17: "caar" should be --car--.

Column 28, line 35: --EXAMPLE 54-- should be inserted.

line 62: "were" should be --was--.

Column 33, line 15: After "3.1" add --g.--.

line 23: "thylamaine" should be --thylamine--.

Column 34, line 9: "dicloromethane" should be --dichloromethane--.

UNITED STATES PATENT OFFICE
CERTIFICATE OF CORRECTION

Patent No. 3,953,428　　　　　　　　Dated April 27, 1976

Inventor(s) Masuo Murakami, et al　　　　Page 3 of 6

It is certified that error appears in the above-identified patent and that said Letters Patent are hereby corrected as shown below:

Column 35, line 46:　"away" should be --off--.

line 49:　After "acidify" insert --the solution--.

line 50:　"orgaic" should be --organic--.

line 52:　After "then" add --an--.

line 52:　"of" should be --containing--.

Column 36, line 36:　"away" should be --off--;

line 36:　After "provide" add --a--.

line 41:　After "of" (2nd occurrence) add --a--.

line 42:　"of" should be --containing--.

line 56:　After "then" add --a-- line 56:　"of" should be --containing--.

line 57:　"a" should be cancelled.

UNITED STATES PATENT OFFICE
CERTIFICATE OF CORRECTION

Patent No. 3,953,428    Dated April 27, 1976

Inventor(s)  Masuo Murakami, et al    Page 4 of 6

It is certified that error appears in the above-identified patent and that said Letters Patent are hereby corrected as shown below:

Column 40, line 30: Delete "the".

last line: After "1H," insert --s--.

Column 41, line 56: "4.08" should be --4.03--.

Column 45, line 48: "triethyllamine" should be

--triethylamine--.

Column 46, line 2: "wit" should be --with--.

Column 49, line 2: "62 lactam" should be --$\beta$ lactam)--.

line 68: "&" should be deleted.

UNITED STATES PATENT OFFICE
CERTIFICATE OF CORRECTION

Patent No. 3,953,428  Dated April 27, 1976

Inventor(s) Masuo Murakami, et al     Page 5 of 6

It is certified that error appears in the above-identified patent and that said Letters Patent are hereby corrected as shown below:

Column 51, line 6: "N" should be --$\underline{N}$--.

line 9: "N" should be --$\underline{N}$--.

line 25: "caroxylate" should be --carboxylate--.

line 60: "a." should be --(a).--.

Column 52, line 19: "(Dhd" should be --D--.

line 63: "b." should be --(b).--.

Column 53, line 20: "N" should be --$\underline{N}$--.

line 24: "N" should be --$\underline{N}$--.

line 65: "a." should be --(a).--

Column 55, line 12: "b." should be --(b).--.

Column 56, line 35: "tempertures" should be --temperatures--.

line 61: "(H,s" should be --(1H,s--.

Column 57, line 51: "(4.6" should be --(4,6--.

UNITED STATES PATENT OFFICE
CERTIFICATE OF CORRECTION

Patent No. 3,953,428　　　　　　Dated April 27, 1976

Inventor(s)　Masuo Murakami, et al　　　Page 6 of 6

It is certified that error appears in the above-identified patent and that said Letters Patent are hereby corrected as shown below:

Column 59, line 33:　"a." should be --(a).--.

line 47:　After "then" add --the--.

Column 60, line 42:　"b." should be --(b).--.

Column 61, lines 54-55:　"temperaure" should be --temperature--.

Column 61, line 65:　"crystal was" should be --crystals were--.

Column 62, line 44:　"b." should be --(b).--.

Column 63, line 37:　"a." should be --(a).--.

Column 64, line 53:　"b." should be --(b).--.

Column 65, line 58:　"a." should be --(a).--.

Column 66, line 2:　"precpitate" should be --precipitate--.

line 44:　"1.88" should be --6.88--.

line 63:　"b." should be --(b).--.

line 66:　"N" should be --$\underline{N}$--.

Signed and Sealed this

First Day of February 1977

[SEAL]

Attest:

RUTH C. MASON　　　　　　　C. MARSHALL DANN
Attesting Officer　　　　　Commissioner of Patents and Trademarks

UNITED STATES PATENT OFFICE
CERTIFICATE OF CORRECTION

Patent No. 3,953,428    Dated April 27, 1976

Inventor(s) Masuo Murakami, et al

It is certified that error appears in the above-identified patent and that said Letters Patent are hereby corrected as shown below:

In the Abstract of the Disclosure, 2nd column, in the structural formulae (1), (2), (3) and (4): a line is missing on the right-hand side of the benzene ring through the double bond and should be inserted to appear as follows: 

In the Abstract, 2nd column, line 2: Change "the position" to --the 3-position--.

Column 4, line 10: Cancel "effect".

Column 47, line 64: "magentic" should be --magnetic--.

Column 48, line 62: "ethylhaxanoate" should be --ethylhexanoate--.

Column 49, line 4: "megnetic" should be --magnetic--.

Column 50, line 4: "wad" should be --was--.

line 14: "magentic" should be --magnetic--.

Column 51, line 25: "caroxylate" should be --carboxylate--.

UNITED STATES PATENT OFFICE
CERTIFICATE OF CORRECTION

Patent No. 3,953,428    Dated April 27, 1976

Inventor(s) Masuo Murakami, et al    Page 2 of 2

It is certified that error appears in the above-identified patent and that said Letters Patent are hereby corrected as shown below:

In column 29, line 65: After "solution" add --thus--.

In column 49, line 63: "of" (2nd occurrence) should be --in a--.

Signed and Sealed this

Twenty-second Day of March 1977

[SEAL]

Attest:

RUTH C. MASON
Attesting Officer

C. MARSHALL DANN
Commissioner of Patents and Trademarks